US012402955B2

(12) United States Patent
Perez Filho et al.

(10) Patent No.: US 12,402,955 B2
(45) Date of Patent: Sep. 2, 2025

(54) EXTENDED-REALITY VISUALIZATION OF ENDOVASCULAR NAVIGATION

(71) Applicant: Regents of the University of Minnesota, Minneapolis, MN (US)

(72) Inventors: Enio T. Perez Filho, Minneapolis, MN (US); Braden Eliason, Minneapolis, MN (US); Reza Talaie, Plymouth, MN (US); Aaron Koenigsberg, Farmington, MN (US); Jafar Golzarian, Plymouth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 342 days.

(21) Appl. No.: 18/003,295

(22) PCT Filed: Jun. 29, 2021

(86) PCT No.: PCT/US2021/070787
§ 371 (c)(1),
(2) Date: Dec. 23, 2022

(87) PCT Pub. No.: WO2022/006586
PCT Pub. Date: Jan. 6, 2022

(65) Prior Publication Data
US 2023/0248441 A1    Aug. 10, 2023

Related U.S. Application Data

(60) Provisional application No. 63/200,007, filed on Feb. 9, 2021, provisional application No. 63/045,542, filed on Jun. 29, 2020.

(51) Int. Cl.
*A61B 34/20* (2016.01)
*A61B 90/00* (2016.01)

(52) U.S. Cl.
CPC ............ *A61B 34/20* (2016.02); *A61B 90/361* (2016.02)

(58) Field of Classification Search
CPC .................. A61B 34/20; A61B 90/361; A61B 2034/2048; A61B 2034/105;
(Continued)

(56) References Cited

U.S. PATENT DOCUMENTS 6,368,285 B1   4/2002 Osadchy et al.
6,725,079 B2   4/2004 Zuk et al.
(Continued)

FOREIGN PATENT DOCUMENTS

WO    2013116140 A1    8/2013

OTHER PUBLICATIONS

Battisti et al., "Fiber Bragg gratings-based sensing for real-time needle tracking during MR-guided brachytherapy", Medical Physics, vol. 43, No. 10, Oct. 2016, 10 pp., doi: 10.1118/1.4961743.
(Continued)

*Primary Examiner* — Bo Joseph Peng
(74) *Attorney, Agent, or Firm* — Shumaker & Sieffert, P.A.

(57) ABSTRACT

Techniques are disclosed for extended-reality (XR) visualization of a flexible medical tool. In one example, sensor(s), disposed near a distal portion of a flexible shaft of a medical tool configured for insertion into a patient, sense values indicative of a pose of the medical tool with respect to an EM field. A computing device adjusts, based on the sensed values, a relative alignment between the medical tool, an internal anatomy of the patient, and an exterior of the body of the patient. The computing device generates, based on the computed relative alignment between the medical tool, the internal anatomy, and the exterior of the body, XR content comprising a visual representation of the medical tool within (Continued)

the patients internal anatomy, and outputs the XR content for display to a user so as to simulate a current pose of the medical tool relative to the body of the patient.

20 Claims, 14 Drawing Sheets

(58) Field of Classification Search
CPC .... A61B 2034/2051; A61B 2034/2055; A61B 2034/2061; A61B 2090/365; A61B 2090/372; A61B 2090/376; A61B 2090/3966; A61B 2090/502
See application file for complete search history.

(56) References Cited

U.S. PATENT DOCUMENTS

| | | | |
|---|---|---|---|
| 7,781,724 B2 | 8/2010 | Childers et al. | |
| 8,050,523 B2 | 11/2011 | Younge et al. | |
| 8,287,481 B1 | 10/2012 | Kahn et al. | |
| 8,298,147 B2 | 10/2012 | Huennekens et al. | |
| 8,346,344 B2 | 1/2013 | Pfister et al. | |
| 8,347,738 B2 | 1/2013 | Tung et al. | |
| 8,628,491 B2 | 1/2014 | Kahn et al. | |
| 8,852,130 B2 | 10/2014 | Govari | |
| 9,072,596 B1 | 7/2015 | Kahn et al. | |
| 9,636,040 B2 | 5/2017 | Duindam et al. | |
| 9,785,246 B2 | 10/2017 | Isaacs et al. | |
| 9,788,909 B2 | 10/2017 | Larkin et al. | |
| 9,795,319 B2 | 10/2017 | Lavallee et al. | |
| 9,901,406 B2 | 2/2018 | State et al. | |
| 10,016,148 B2* | 7/2018 | Li | A61B 34/20 |
| 10,092,215 B2 | 10/2018 | Salamini et al. | |
| 10,123,755 B2* | 11/2018 | Walker | A61B 8/12 |
| 10,139,920 B2 | 11/2018 | Isaacs et al. | |
| 10,143,526 B2* | 12/2018 | Walker | A61B 34/30 |
| 10,188,467 B2 | 1/2019 | Razzaque et al. | |
| 10,194,131 B2 | 1/2019 | Casas | |
| 10,271,909 B2 | 4/2019 | Guthart et al. | |
| 10,314,559 B2 | 6/2019 | Razzaque et al. | |
| 10,405,927 B1 | 9/2019 | Lang | |
| 10,444,855 B2 | 10/2019 | Isaacs et al. | |
| 10,478,255 B2 | 11/2019 | West et al. | |
| 10,481,704 B2 | 11/2019 | Parazynski | |
| 10,788,791 B2 | 9/2020 | Gellman et al. | |
| 2002/0198588 A1 | 12/2002 | Armstrong et al. | |
| 2005/0020963 A1 | 1/2005 | Gabal | |
| 2008/0013809 A1 | 1/2008 | Zhu et al. | |
| 2008/0091101 A1 | 4/2008 | Velusamy et al. | |
| 2010/0249506 A1 | 9/2010 | Prisco | |
| 2012/0220879 A1 | 8/2012 | Fandrey et al. | |
| 2014/0189508 A1 | 7/2014 | Granchi et al. | |
| 2014/0282008 A1 | 9/2014 | Verard et al. | |
| 2016/0324580 A1 | 11/2016 | Esterberg | |
| 2017/0014194 A1 | 1/2017 | Duindam et al. | |
| 2017/0119481 A1* | 5/2017 | Romo | A61B 1/00096 |
| 2017/0367771 A1 | 12/2017 | Tako et al. | |
| 2018/0116732 A1 | 5/2018 | Lin et al. | |
| 2018/0185100 A1 | 7/2018 | Weinstein et al. | |
| 2018/0200018 A1 | 7/2018 | Silva et al. | |
| 2018/0214138 A9* | 8/2018 | Prisco | A61B 17/3478 |
| 2018/0279852 A1* | 10/2018 | Rafii-Tari | G16H 40/63 |
| 2018/0303563 A1 | 10/2018 | West et al. | |
| 2019/0155439 A1* | 5/2019 | Mukherjee | A63F 13/214 |
| 2019/0246088 A1 | 8/2019 | Casas | |
| 2019/0328458 A1* | 10/2019 | Shmayahu | A61B 5/064 |
| 2020/0275988 A1 | 9/2020 | Johnson et al. | |

OTHER PUBLICATIONS

Clarke et al., "Virtual Reality Imaging with Real-Time Ultrasound Guidance for Facet Joint Injection: A Proof of Concept", International Anesthesia Research Society, vol. 110, No. 5, Dec. 29, 2009, pp. 1461-1463.
Heinrich et al., "HoloInjection: augmented reality support for CT-guided spinal needle injections", Healthcare Technology Letters, vol. 6, No. 6, Nov. 26, 2019, pp. 165-171, doi: 10.1049/htl.2019.0062.
International Preliminary Report on Patentability from International Application No. PCT/US2021/070787 dated Jan. 12, 2023, 9 pp.
International Search Report and Written Opinion of International Application No. PCT/US2021/070787 dated Oct. 22, 2022, 9 pp.
Kamarudin et al., "Augmented Reality, Virtual Reality, and Mixed Reality in Medical Education: A Comparative Web of Science Scoping Review", Preprints, Apr. 29, 2019, 10 pp., doi:10.20944/preprints201904.0323.v1.
Liu et al., "An augmented reality system for image guidance of transcatheter procedures for structural heart disease", PLoS One, vol. 14, No. 7, e0219174, PubMed, Jul. 1, 2019, 16 pp., doi: 10.1371/journal.pone.0219174. eCollection 2019.
Solbiati et al., "Augmented reality for interventional oncology: proof-of-concept study of a novel high-end guidance system platform", European Radiology Experimental, vol. 2, No. 18, Jul. 31, 2018, 9 pp., https://doi.org/10.1186/s41747-018-0054-5.

* cited by examiner

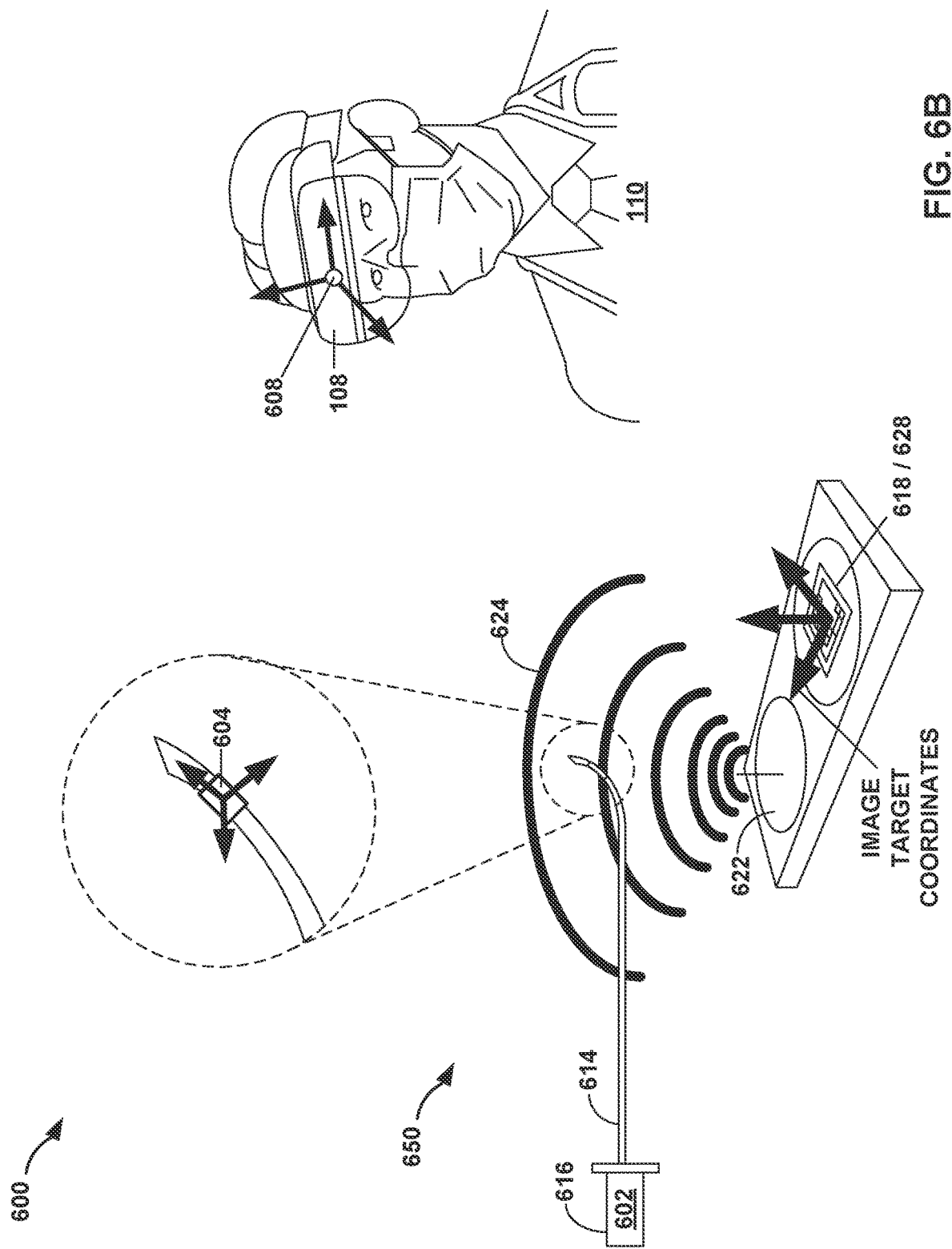

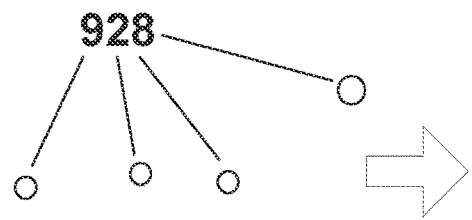
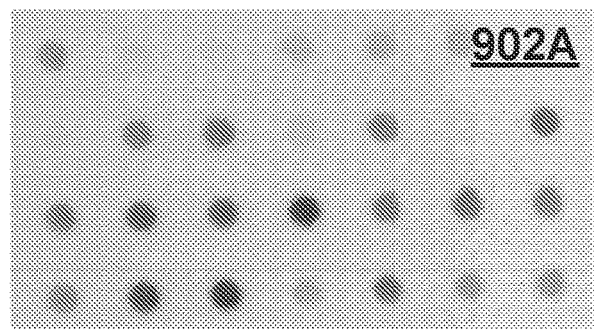
FIG. 9A
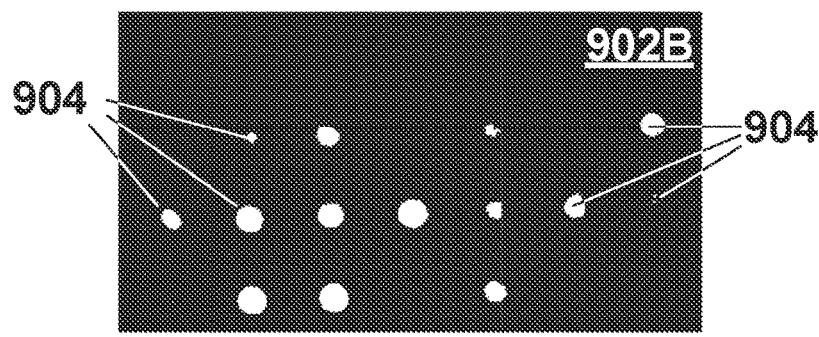
FIG. 9B
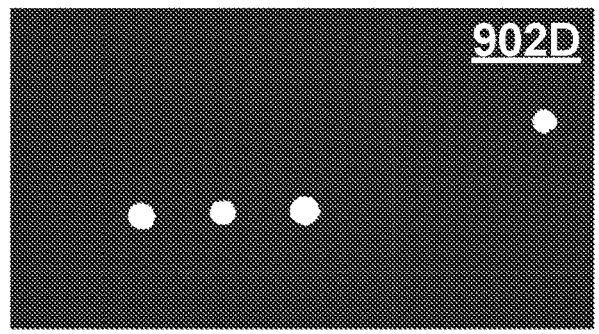
FIG. 9C
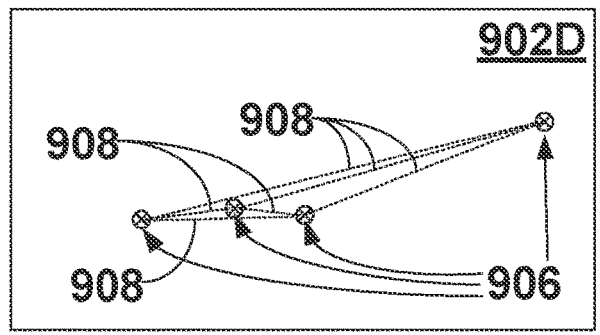
FIG. 9D

EXTENDED-REALITY VISUALIZATION OF ENDOVASCULAR NAVIGATION

This application claims the benefit of U.S. Provisional Patent Application No. 63/045,542, entitled "AUGMENTED REALITY VISUALIZATION OF ENDOVASCULAR NAVIGATION," and filed Jun. 29, 2020, and also claims the benefit of U.S. Provisional Patent Application No. 63/200,007, entitled "EXTENDED-REALITY VISUALIZATION OF ENDOVASCULAR NAVIGATION," and filed Feb. 9, 2021. The entire contents of U.S. Provisional Patent Application Nos. 63/045,542 and 63/200,007 are incorporated herein by reference.

TECHNICAL FIELD

This disclosure generally relates to systems for visualizing procedures involving implantable medical articles.

BACKGROUND

Clinicians use medical imaging techniques to visualize the interior of a body of a patient for clinical analysis and medical treatment. Medical imaging may be used to implement image-guided clinical procedures, in which a clinician uses preoperative or intraoperative images of the patient to guide the positioning and use of medical instruments. Systems for performing image-guided clinical procedures may use cameras, ultrasonic imaging, electromagnetic imaging, X-ray imaging, or other types of imaging to capture and relay the position of medical tools with respect to the anatomy of the patient. Typically, a clinician performs such image-guided clinical procedures in real-time. For example, fluoroscopy is an example medical imaging technique that uses X-rays to obtain real-time moving images of the interior of the body of the patient. A clinician may use images obtained by fluoroscopy to visualize, for example, a medical tool implanted within the patient and guide navigation of the medical tool to a target site within the patient's anatomy.

SUMMARY

Techniques are disclosed for extended-reality (XR) visualization of a pose (e.g., a relative position and orientation) of a flexible medical tool configured for insertion into a patient. The techniques set forth herein may enable XR visualization of a position of medical tool within an interior anatomy of a patient and with respect to an exterior anatomy of the patient, such as during a clinical procedure. In some examples, the medical tool is a catheter, a needle, a sheath, a guidewire, or a transjugular intrahepatic portosystemic shunt (TIPS) set.

In one example of the techniques of the disclosure, one or more electromagnetic (EM) sensor(s) of an EM sensor system are disposed near a distal portion of a flexible shaft of the medical tool. The EM sensors generate signals indicative of a magnitude or strength of an EM field generated by an EM source of the sensor system. Processing circuitry receives the signals indicative of the magnitude of the EM field and determines a pose of the one or more EM sensors, and therefore a pose of the distal portion of the flexible shaft of the medical tool. The processing circuitry adjusts a three-dimensional (3-D) model representation of the medical tool based on the determined pose of the one or more EM sensors.

The processor receives first image data depicting at least a portion of an internal anatomy of the body of the patient and an internal imaging target. The processor further receives second image data depicting an external imaging target and/or a portion of an exterior of the body of the patient. The processor correlates the signals indicative of the magnitude or strength of the EM field, the first image data, and the second image data to one another to determine a relative alignment between the pose of the one or more EM sensors, a pose of the external imaging target, and a pose of the internal imaging target. In some examples, a pose of the EM sensor system, the internal imaging target, and the external imaging target are positioned at predetermined distances from one another such that the processing circuitry may map the signals indicative of the magnitude of the EM field, the internal imaging target depicted in the first image data, and the external imaging target depicted in the second image data to map the pose of the one or more EM sensors, the pose of the external imaging target, and the pose of the internal imaging target to one another. The computing device generates, based on the determined relative alignment, XR content comprising a visual representation of the medical tool within the at least a portion of the internal anatomy of the body. The processor output the XR content to an XR device, such as a head-mounted display (HMD), which displays the XR content to a user, such as overlaid onto a view of the patient's body so as to simulate a real-time position and orientation of the medical tool.

The techniques of the disclosure may provide specific improvements to the computer-related field of XR visualization systems that have practical applications. For example, the techniques described herein provide for surgical guidance systems that may be significantly more accurate and/or precise than previous systems. More specifically, the techniques described herein include computer-implemented methods for defining and precisely aligning multiple distinct coordinate systems based on highly accurate sensor data, thereby enabling graphical visualizations representative of a patient's internal anatomy and a medical tool aligned according to their real-world positions and orientations with respect to each other in real-time.

In one example, this disclosure describes a method including: receiving, by processing circuitry and from one or more electromagnetic (EM) sensors of an EM sensor system, signals indicative of a magnitude of an EM field generated by an EM source of the EM sensor system, wherein the one or more EM sensors are disposed at a distal portion of a flexible shaft of a medical tool configured for insertion into a body of a patient; determining, by the processing circuitry and based on the signals indicative of the magnitude of the EM field, a pose of the one or more EM sensors; adjusting, by the processing circuitry and based on the determined pose of the one or more EM sensors, a three-dimensional (3-D) model representation of the medical tool; receiving, by the processing circuitry, first image data depicting at least a portion of an internal anatomy of the body of the patient and an internal imaging target; receiving, by the processing circuitry, second image data depicting an external imaging target; determining, by the processing circuitry and based on the signals indicative of the magnitude of the EM field, the first image data, and the second image data, a relative alignment between the pose of the one or more EM sensors, a pose of the external imaging target, and a pose of the internal imaging target; generating, by the processing circuitry and based on the determined relative alignment, extended reality (XR) content comprising a visual representation of the medical tool within the at least a portion of the internal anatomy of the body; and outputting, by the processing circuitry, the XR content for display on an XR device.

In another example, this disclosure describes processing circuitry of a computing device configured to receive, from one or more electromagnetic (EM) sensors of an EM sensor system, signals indicative of a magnitude of an EM field generated by an EM source of the EM sensor system, wherein the one or more EM sensors are disposed at a distal portion of a flexible shaft of a medical tool configured for insertion into a body of a patient; determine, based on the signals indicative of the magnitude of the EM field, a pose of the one or more EM sensors; adjust, based on the determined pose of the one or more EM sensors, a three-dimensional (3-D) model representation of the medical tool; receive first image data depicting at least a portion of an internal anatomy of the body of the patient and an internal imaging target; receive second image data depicting an external imaging target; determine, based on the signals indicative of the magnitude of the EM field, the first image data, and the second image data, a relative alignment between the pose of the one or more EM sensors, a pose of the external imaging target, and a pose of the internal imaging target; generate, based on the determined relative alignment, extended reality (XR) content comprising a visual representation of the medical tool within the at least a portion of the internal anatomy of the body; and output the XR content for display on an XR device.

In another example, this disclosure describes a system comprising: a medical tool configured for insertion into a body of a patient; an electromagnetic (EM) sensor system comprising: an EM source configured to generate an EM field; and one or more EM sensors configured to generate signals indicative of a magnitude of the EM field, wherein the one or more EM sensors are disposed at a distal portion of a flexible shaft of the medical tool; processing circuitry configured to: receive, from the one or more EM sensors, the signals indicative of the magnitude of the EM field; determine, based on the signals indicative of the magnitude of the EM field, a pose of the one or more EM sensors; adjust, based on the determined pose of the one or more EM sensors, a three-dimensional (3-D) model representation of the medical tool; receive first image data depicting at least a portion of an internal anatomy of the body of the patient and an internal imaging target; receive second image data depicting an external imaging target; determine, based on the signals indicative of the magnitude of the EM field, the first image data, and the second image data, a relative alignment between the pose of the one or more EM sensors, a pose of the external imaging target, and a pose of the internal imaging target; generate, based on the determined relative alignment, extended reality (XR) content comprising a visual representation of the medical tool within the at least a portion of the internal anatomy of the body; and the XR device, where in the XR device is configured to display the XR content to a user.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIGS. 6A and 6B are conceptual diagrams illustrating another example system for generating XR content for visualizing a flexible medical tool, in accordance with techniques of this disclosure.

FIGS. 9A-9D are conceptual diagrams illustrating the technique of FIG. 8A.

Like reference characters refer to like elements throughout the figures and description.

DETAILED DESCRIPTION

Figure 1:
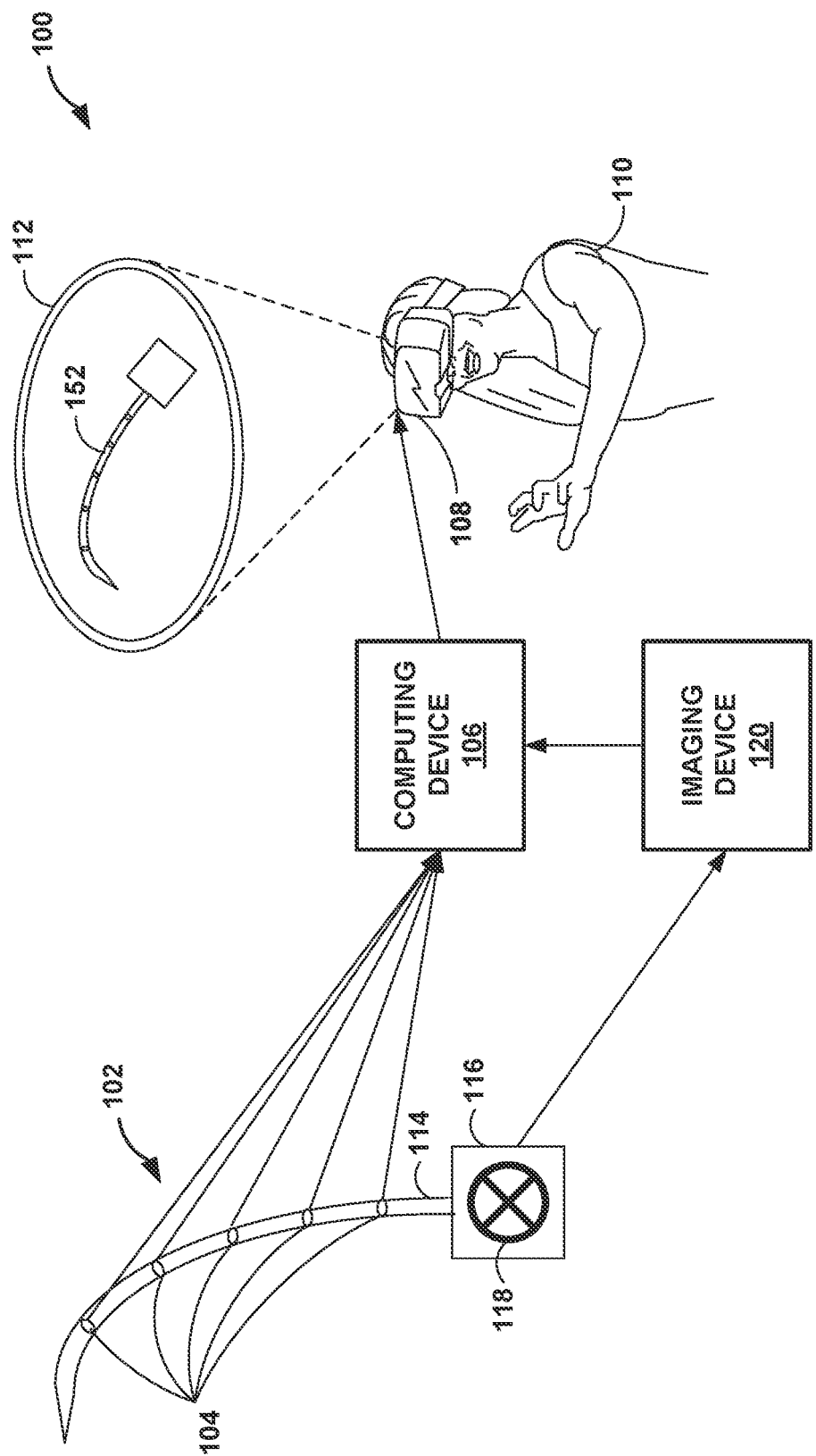
FIG. 1 is a block diagram illustrating an example system for generating extended-reality (XR) content for visualizing a flexible medical tool.

Clinicians typically review a pre-operative computerized tomography (CT) scan of a patient to build a conceptual model of the patient's anatomy prior to performing the operation. The clinician may use other imaging modalities, such as ultrasound, during the operation (e.g., "intraoperatively") to direct a plane of view (e.g., in examples in which the ultrasound imagery corresponds to a plane) within which a medical tool, such as a needle, sheath, or catheter, is traveling. Current imaging modalities, such as fluoroscopy and ultrasound, only provide operators with a two-dimensional (2-D) view of the field. These techniques have varying degrees of success, and depend on the clinician's ability to mentally reconstruct a 3-D model of the patient's internal anatomy, e.g., based on CT-scan imagery.

"Artificial" reality or "extended" reality (XR) systems are becoming increasingly ubiquitous with applications in many fields such as computer gaming, health and safety, industry (e.g., manufacturing, agriculture, etc.), and education. In general, XR is a form of reality that has been adjusted in some manner before presentation to a user. XR may include, e.g., a virtual reality (VR), an augmented reality (AR), a mixed reality (MR), a hybrid reality, or any combination and/or derivatives thereof. Typical XR systems include one or more devices for rendering and displaying content to users. As one example, an XR system may incorporate a head-mounted display (HMD) worn by a user and configured to output XR content to the user. In particular, the XR system typically computes a current pose (e.g., relative position and orientation) within a frame of reference, such as relative to (e.g., from a point of view of) the HMD, and selectively renders XR content for display to the user based on the current pose. The XR content may include content that is entirely artificial, or content that includes some artificially generated content combined with "captured" content, such as real-world video and/or images.

Techniques are described herein for generating XR content for visualizing a real-time position and orientation of a medical tool, for example, while the medical tool is inserted within a patient during a clinical procedure. In one example, the medical tool includes a Transjugular Intrahepatic Portosystemic Shunt (TIPS) set. The medical tool may incorporate a modified sheath (which may be referred to herein as a "catheter") and/or a puncture needle, outfitted with one or more sensors along a flexible shaft. In one implementation, the sheath or needle is outfitted with (e.g., is mechanically coupled to) sensors. In other implementations, the sensors may be printed directly onto the sheath and/or needle. The sensors along the shaft provide position information to imaging-overlay software executed by a computing device, which uses the position information to alter an XR image overlay of the medical tool so as to correspond to the actual physical position and/or orientation of the needle and/or sheath. The medical tool further incorporates a fiducial marker (also referred to herein as an "imaging target"), which may be positioned at a base of the medical tool. The function of the imaging target is to provide a point of reference to the XR display device, such as a headset or additional cameras located in the periphery of the surgical field, with a fiducial or reference point from which to position the XR-image overlay. Although described herein with respect to TIPS procedures, the techniques of this disclosure may be applied to any suitable medical procedure including, but not limited to, a prostate artery embolization procedure, a genicular artery embolization procedure, or the like.

In some examples, the techniques described herein include using 3-D information obtained from preoperative CT scans in order to allow a clinician to better understand spatial relationships of target anatomy of a patient. The techniques of the disclosure may have many other commercial applications, which may include percutaneous endovascular targeting, XR-guided endovascular navigation, or percutaneous biopsy tracking of a flexible needle.

FIG. 1 is a block diagram illustrating example system 100 for generating XR content 112 for visualizing flexible medical tool 102. System 100 includes medical tool 102, imaging device 120, computing device 106, and XR head-mounted display (HMD) 108.

Medical tool 102 is typically a flexible medical instrument capable of insertion or implantation within a patient. In some examples, medical tool 102 comprises a catheter, a needle, or a sheath. Medical tool 102 includes flexible shaft 114 and base 116. A plurality of sensors 104 are disposed longitudinally along flexible shaft 114. Each of the plurality of sensors 104 is configured to sense a plurality of values. Each value of the plurality of values is indicative of a change in a position of a respective portion of shaft 114 at which a corresponding sensor 104 is disposed, wherein the change in position is measured from a "calibration" position of the respective portion of shaft 114.

In some examples, base 116 of medical tool 102 is a base of a modified puncture needle. Base 116 is configured to receive signals from sensors 104 disposed on shaft 114, and includes communication circuitry for communicating sensor signals from sensors 104 to computing device 106 and/or HMD 108. Furthermore, base 116 may include, or act as, a fiducial marker 118 from which computing device 106 overlays a digital representation 152 of medical tool 102, as described in more detail below.

Imaging device 120 includes, as examples, a camera or a video-capture device. Imaging device 120 generates one or more images of medical tool 102 within the 3-D environment. In some examples, imaging device 120 generates images that depict or otherwise include fiducial marker 118 affixed to base 116 of medical tool 102.

Computing device 106 includes processing circuitry and memory. In some examples, the processing circuitry of computing device 106 includes one or more processors, such as one or more microprocessors, digital signal processors (DSPs), application-specific integrated circuits (ASICs), field-programmable gate arrays (FPGAs), or any other equivalent integrated or discrete logic circuitry, as well as any combinations of such components. In some examples, the memory of computing device 106 includes random-access memory (RAM), read-only memory (ROM), programmable read-only memory (PROM), erasable programmable read-only memory (EPROM), electronically erasable programmable read-only memory (EEPROM), or flash memory, and includes executable instructions for causing the one or more processors to perform the actions attributed to them, as described herein. Further, this memory may be implemented entirely in hardware, software, or a combination thereof.

Medical tool 102 transmits, to computing device 106, the values sensed by the plurality of sensors 104. Computing device 106 receives the plurality of values sensed by the plurality of sensors 104 and adjusts, based on the values sensed by the plurality of sensors 104, a 3-D model representation 152 of medical tool 102. For example, computing device 106 may rotate, translate, transform, stretch, warp, or bend a 3-D model representation 152 of medical tool 102 in order to approximate or match a real-world shape, configuration, or position of medical tool 102 as sensed by sensors 104. For example, sensors 104 may detect a flexing or bending of medical tool 102 away from a "calibration" configuration of medical tool 102.

Computing device 106 uses the images of medical tool 102 from imaging device 120 in order to compute a pose of medical tool 102 within the 3-D environment. For example, computing device 106 uses images depicting fiducial marker 118 positioned on medical tool 102 as a fiducial reference point to localize a position and/or orientation of medical tool 102 within a 3-D, real-world environment with respect to the patient. Computing device 106 uses the adjusted 3-D model representation of medical tool 102 and the images of medical tool 102 from imaging device 120 to generate XR content 112 including a visual representation 152 of medical tool 102 within the 3-D environment. In other words, computing device 106 may execute software code that interprets the information from sensors 104 to create an altered digital structure representing medical tool 102. Computing device 106 may alter a digital replica or model of medical tool 102 to conform to the real-world physical structure of medical tool 102, such as based on the information provided by sensors 104 located along shaft 114. For example, XR content 112 may include a visual representation 152 of medical tool 102 (e.g., the adjusted 3-D model representation of medical tool 102) overlaid upon an image of the real-world environment, so as to represent a real-world position and shape of medical tool 102 within a body of the patient.

Computing device 106 outputs the XR content to a display device for display to user 110. As depicted in the example of FIG. 1, the display device includes head-mounted display (HMD) 108. In other examples, the display may be a computer monitor, mobile device, television, or other type of stationary, screen-mounted display.

Figure 2:
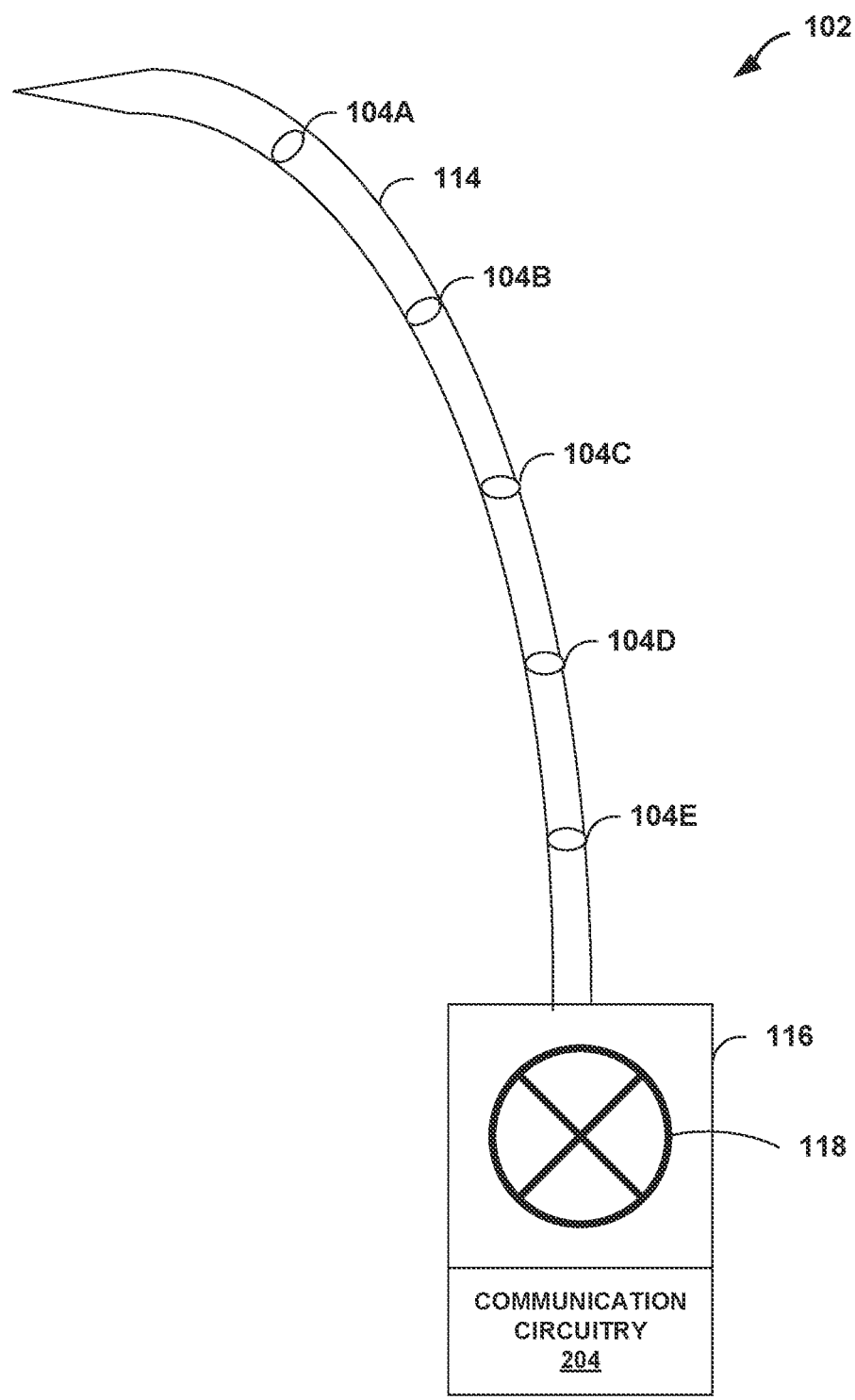
FIG. 2 is a block diagram illustrating the flexible medical tool of FIG. 1 in further detail.

FIG. 2 is a block diagram illustrating flexible medical tool 102 of FIG. 1 in further detail. In some examples, medical tool 102 includes a catheter. In some examples, medical tool 102 includes a needle and/or a guidewire. As depicted in FIG. 2, medical tool 102 includes flexible shaft 114 and base 118.

Sensors 104A-104E (collectively referred to hereinafter as "sensors 104") are disposed longitudinally along shaft 114. In some examples, sensors 104 are disposed longitudinally along a centerline axis of flexible shaft 114 (e.g., such as within a core of shaft 114). In some examples, sensors 104 are disposed longitudinally along a first axis parallel to a centerline axis of the flexible shaft (e.g., such as along an exterior sheath of shaft 114). In some examples, sensors 104 are disposed longitudinally along at least a first axis parallel to a centerline axis of the flexible shaft and a second axis parallel to the centerline axis of the flexible shaft and offset from the first axis. For example, two of sensors 104 may be positioned along each portion of shaft 114 and spaced 90 degrees apart so as to measure multiple axes of motion of shaft 114. As another example, three sensors 104 may be positioned along each portion of shaft 114 and spaced 60 degrees apart so as to measure multiple axes of motion of shaft 114. In some examples, a 3-D printer is used to directly print sensors 104 upon shaft 114 of medical tool 102.

Each of sensors 104 senses a flexing or bending of a respective portion of shaft 114 upon which the sensor 104 is disposed. In some examples, sensors 104 include flex sensors capable of sensing a flexing or bending of shaft 114. In some examples, sensors 104 include strain gauges. Sensors 104 may be analog sensors or digital sensors. For example, each of sensors 104 senses a value indicative of a calibration position of the respective portion of the shaft 114 at which the sensor is disposed. Further, each of sensors 104 senses a value indicative of a change in a relative position of a respective portion of shaft 114 at which a corresponding sensor 104 is disposed, as measured from a calibration position of the respective portion of shaft 114. Sensors 104 output values indicative of the change in the position of the respective portion of shaft 114 at which each sensor 104 is disposed, as measured from the calibration position of the respective portion of shaft 114. In some examples, the sensed value is indicative of a displacement of the position of the respective portion of shaft 114 at which the sensor 104 is disposed, as measured from the calibration position of the portion of shaft 114. In some examples, the sensed value is indicative of an angular displacement of the position of the respective portion of shaft 114 at which the sensor 104 is disposed, as measured from the calibration position of the respective portion of shaft 114.

Base 116 includes communication circuitry 204 for transmitting, to computing device 106 (FIG. 1), the values sensed by the plurality of sensors 104. In some examples, communication circuitry 204 communicates with computing device 106 via a wired or wireless connection. Base 116 further includes fiducial marker 118, which computing device 106 may use as a fiducial reference point to localize a position and/or orientation (e.g., a "pose") of medical tool 102 within a 3-D, real-world environment with respect to the patient.

Figure 3:
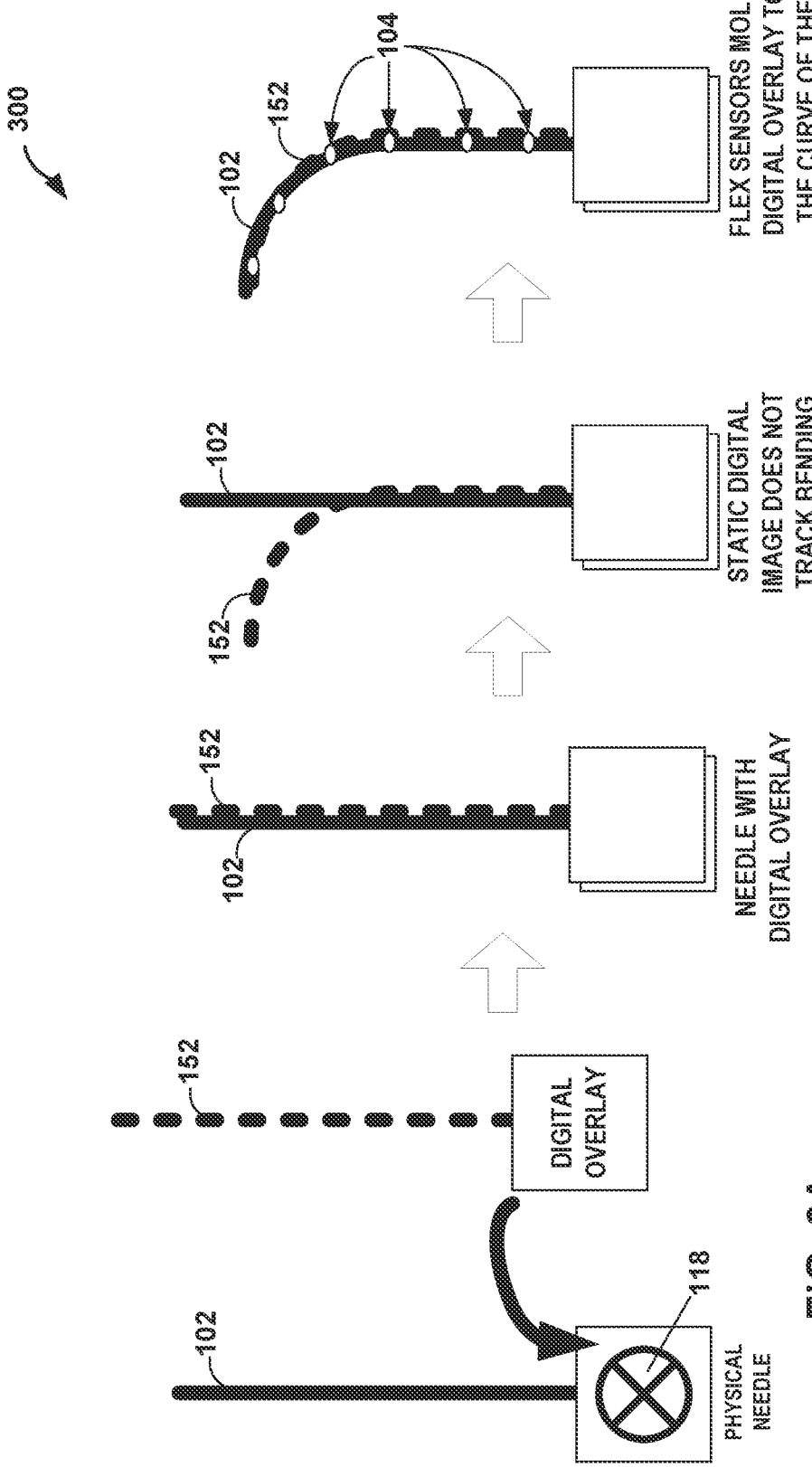
FIGS. 3A-3D are conceptual diagrams illustrating an example technique for generating an XR rendering of the flexible medical tool of FIG. 1.

FIGS. 3A-3D are conceptual diagrams illustrating an example technique for generating an XR rendering 152 of flexible medical tool 102. As depicted in FIGS. 3A and 3B, computing device 106 (FIG. 1) overlays a 3-D model representation 152 of medical tool 102 over an image of medical tool 102. In some examples, computing device 106 uses a fiducial marker or imaging target 118 (which may or may not be fixedly positioned on medical tool 102) in order to localize a position and/or orientation of medical tool 102, so as to correctly position 3-D model 152 overtop of medical tool 102 within the image. As shown in FIGS. 3C and 3D, computing device 106 adjusts a shape of 3-D model representation 152 based on the values sensed by sensors 104 so as to mold 3-D model 152 to approximate or conform to an actual curve or shape of the physical medical tool 102.

Figure 4:
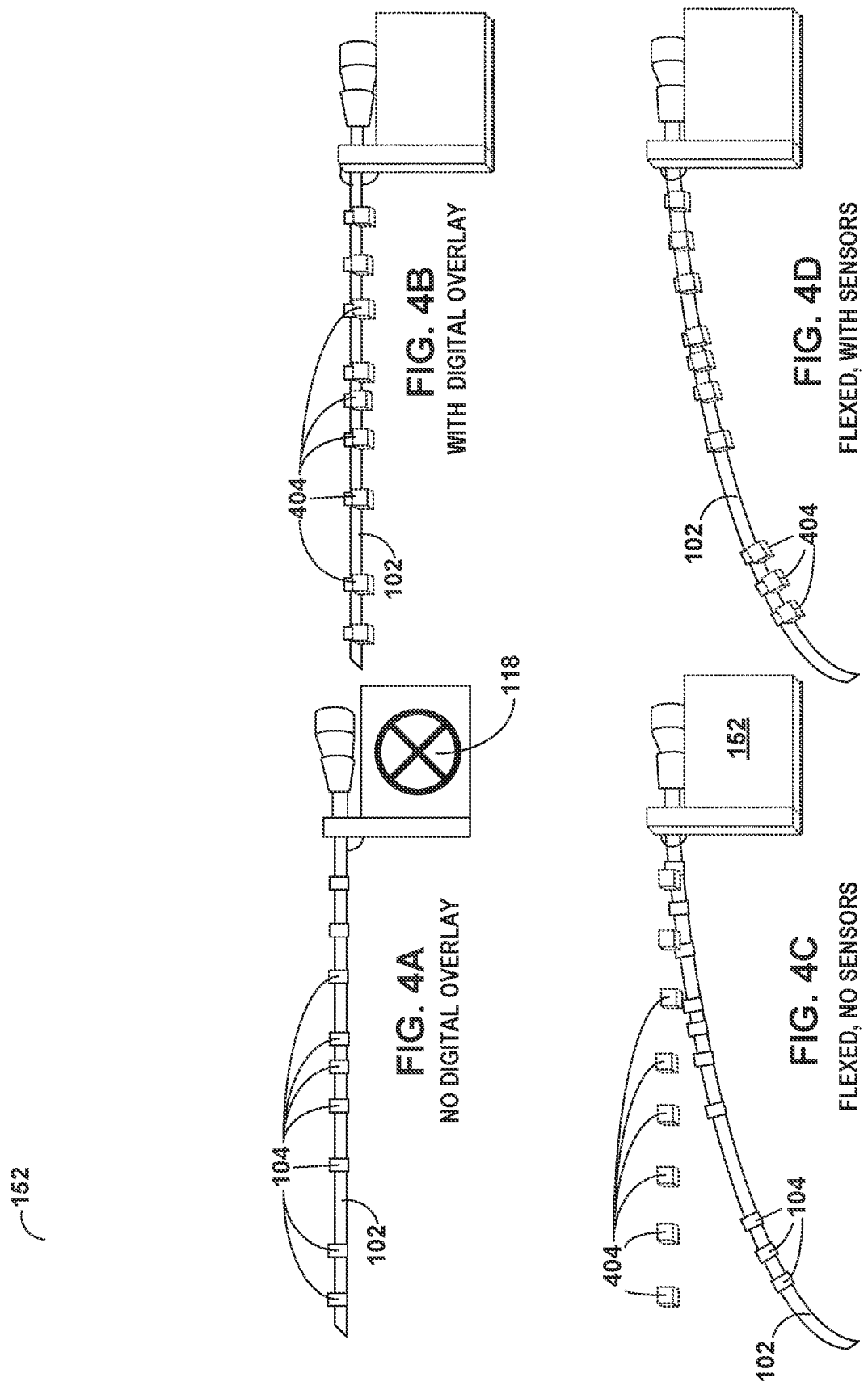
FIGS. 4A-4D are images depicting example XR renderings of the flexible medical tool of FIG. 1.

FIGS. 4A-4D are diagrams depicting example XR renderings of flexible medical tool 102 of FIG. 1. For example, FIGS. 4A-4D depict real-world images of medical tool 102 of FIG. 1, and rendered representations 404 of a relative position of each sensor 104, shown overlaid upon the real-world image. As medical tool 102 flexes and bends in FIG. 4C, the rendered representation of each sensor 104 similarly moves in order to depict the real-world position of the corresponding portion of medical tool 102 (FIG. 4D).

Figure 5:
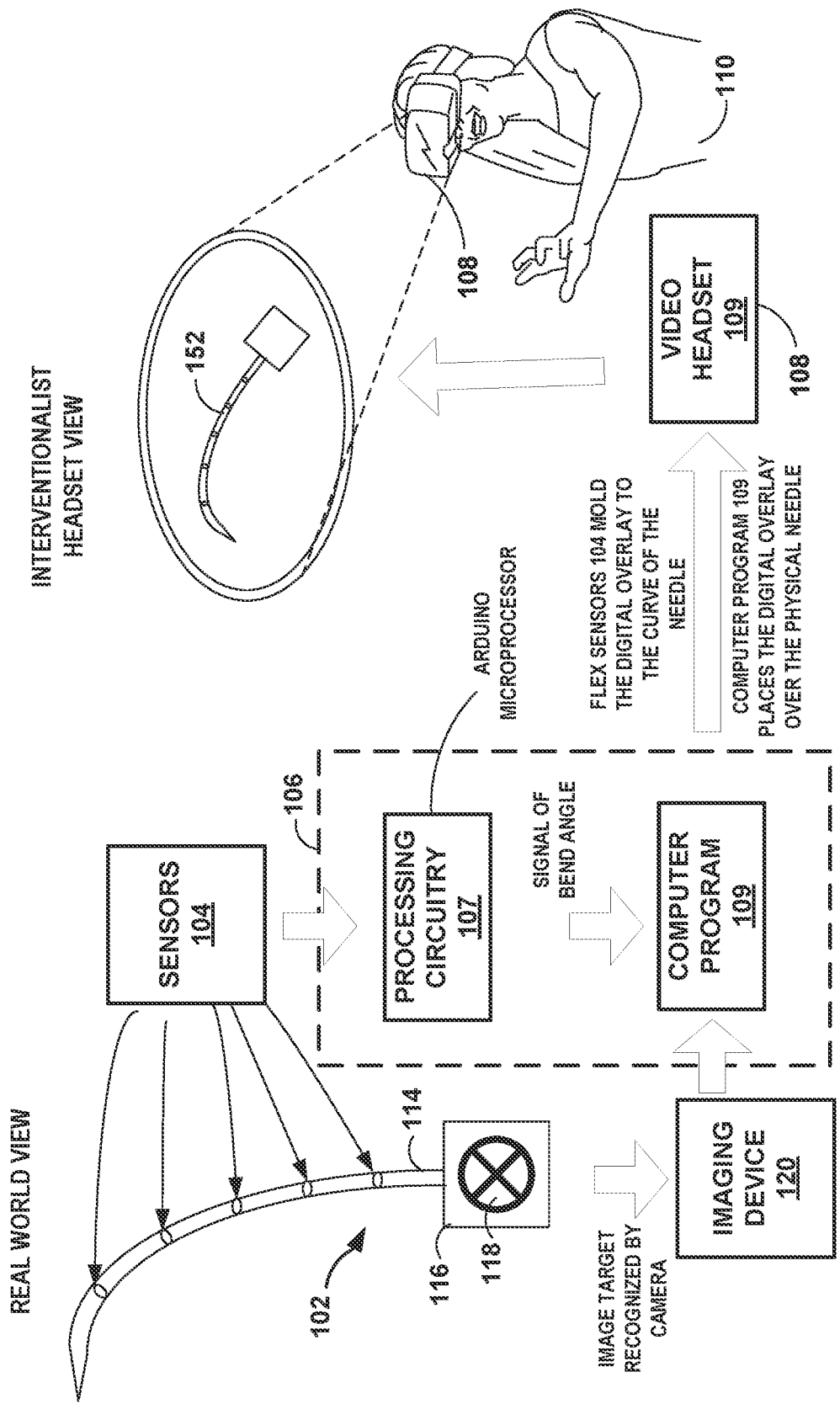
FIG. 5 is a block diagram illustrating another example system for generating XR content for visualizing a flexible medical tool.

FIG. 5 is a block diagram illustrating another example system for generating XR content for visualizing a flexible medical tool 102. In the example of FIG. 5, medical tool 102 includes a plurality of sensors 104 disposed longitudinally along a flexible shaft of medical tool 102. Sensors 104 are configured to sense a plurality of values. Each value of the plurality of sensed values is indicative of a change in a position of a respective portion of the shaft of medical device 102, at which a corresponding sensor 104 of the plurality of sensors 104 is disposed, wherein the change in position is measured from a calibration position of the portion of the shaft of medical device 102.

Processing circuitry 107 of computing device 106 receives the values sensed by the plurality of sensors and adjusts, based on the sensed plurality of values, a three-dimensional (3-D) model representation of medical tool 102. Computing device 106 further receives, from camera 120 (which may be composed of a single unit or a plurality of units providing visualization of the device 102 from a plurality of perspectives), one or more images of medical tool 102 within the 3-D environment. Computing device 106 then executes programming 109 configured to compute, based on the one or more images, a pose of medical tool 102 within the 3-D environment. Computing device 106 generates, based on the adjusted 3-D model representation of medical tool 102 and the computed pose of medical tool 102 within the 3-D environment, a visual representation 152 of medical tool 102 within the 3-D environment. Computing device 106 generates XR content comprising the visual representation of medical tool 102 and outputs the XR content to a display device, such as HMD 108 or a stationary screen, for display to user 110.

Figure 6A:
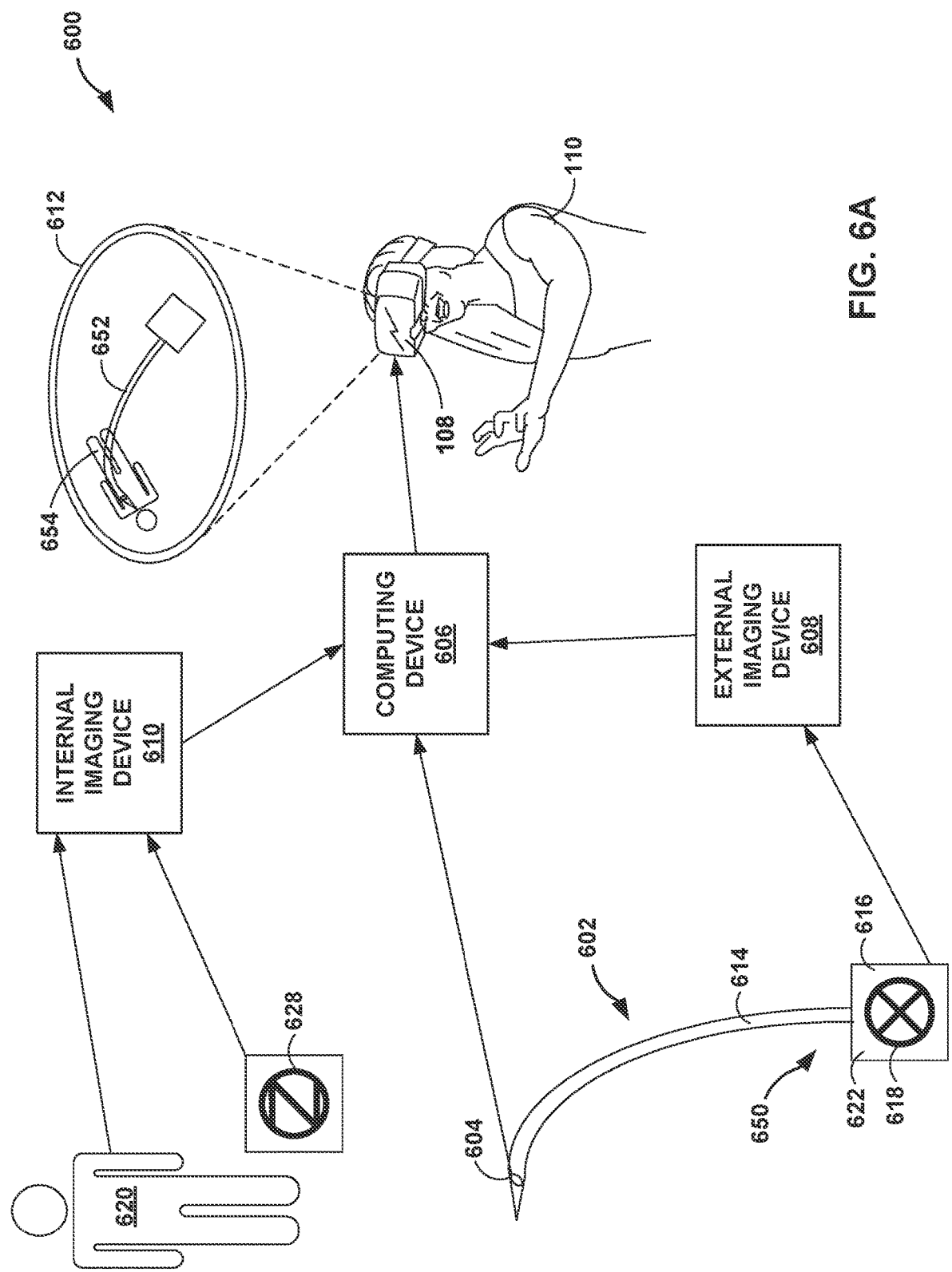

FIGS. 6A and 6B are conceptual diagrams illustrating another example XR system 600 for generating XR content for visualizing a flexible medical tool, in accordance with techniques of this disclosure. System 600 includes medical tool 602, computing device 606, EM sensor system 650, external imaging device 608, internal imaging device 610, and head-mounted display (HMD) 108.

XR system 600 (e.g., via processing circuitry of HMD 108 or another computing device 606) is configured to use three sets of information to generate XR content 612: (1) electromagnetic sensor data captured by EM sensor system 650, indicative of a pose of medical tool 602; (2) "external" image data depicting an exterior of a patient's body 620, as captured by external imaging device 608; and (3) "internal" image data depicting an interior anatomy of the patient's body 620, as captured by internal imaging device 610. XR content 612 includes at least a visual representation 652 of medical tool 602 positioned "accurately" within (e.g., reflecting a real-world and real-time position of medical tool 602 relative to) a visual representation 654 of at least a portion of the internal anatomy of a patient's body 620.

Based on these three sets of data, system 600 is configured to display XR content 612 so as to generate a "transparent view" through the exterior of the patient's body 620 that graphically depicts a real-time simulation of the actual position and orientation of medical tool 602 within the patient's internal anatomy. In examples in which HMD 108 includes a "transparent" visor or lens with XR display functionality, system 600 is configured to display XR content 612 relative to the actual exterior of the patient's body 620, as viewed through the transparent lens. In other examples in which HMD 108 includes an "opaque" display screen (e.g., a virtual-reality headset or goggles), system 600 is configured to generate composite imagery by overlaying XR content 612 onto 2-D imagery depicting the exterior of the patient's body 620, and display the composite imagery on the display screen of HMD 108.

Medical tool 602 is an example of medical tool 102 of FIG. 1, and is typically a flexible medical instrument capable of insertion or implantation within a patient 620. In some examples, medical tool 602 includes a catheter, a needle, a guidewire, or a sheath. Medical tool 602 includes a flexible, elongated shaft 614 and a base 616 at a proximal end of the shaft 614. In some examples, base 616 of medical tool 602 is a base of a modified puncture needle.

System 600 includes one or more "external" imaging targets 618 (also referred to herein as "markers" or "fiducial targets") that are visible to (e.g., detectable by) external imaging device 608, and one or more "internal" imaging targets 628 that are visible to (e.g., detectable by) internal imaging device 610. For instance, as shown in FIG. 6A, external imaging target 618 includes a visually distinct marker that is detectable within external imagery captured by external imaging device 608, which may be an example of imaging device 120 of FIG. 1. For instance, external imaging device 608 may include a forward-facing camera of HMD 108.

Similarly, internal imaging target 628 includes a visually distinct marker that is detectable within internal imagery captured by internal imaging device 610, which may also be an example of imaging device 120 of FIG. 1. For instance, internal imaging device 610 may include an X-ray, MRI machine, CT scanner, or other device configured to generate internal imagery depicting, describing, or otherwise indicative of at least a portion of the internal anatomy of patient 620. In such examples, internal imaging target 628 may be positioned next to (e.g., external to) or within (e.g., internal to) patient 620 as internal imaging device 610 generates the internal imagery. In either example, internal imaging target 628 should be "fixed" with respect to at least one other structure to provide a reliable point of reference. For instance, internal imaging target 628 may be fixed to a surface of a patient bed while internal imaging device 610 captures the internal imagery. In other examples, internal imaging target 628 may include, or may be rigidly coupled to, a "consistent" portion of the patient's internal or external anatomy.

External imaging target(s) 618 and internal imaging target(s) 628 provide reference points within the three datasets used by system 600 to enable 600 to "align" or orient the various datasets relative to one another. For instance, in the example depicted in FIG. 6A (but not in all examples), external imaging target 618 comprises a visual marker that is rigidly coupled to (or defined by) the base 616 of medical tool 602. In such examples, external imaging target 618 provides a "dual" common reference point for alignment of the external imaging data (e.g., based on the position of external imaging target 618 relative to the body of patient 620 when depicted in the external imaging data) with the EM sensor data (e.g., based on the fixed and known position of external imaging target relative to medical tool 602).

In some examples, a single coherent physical object may be configured to provide the dual-reference-point functionality of both external imaging target 618 and internal imaging target 628, e.g., that is visible to both external imaging device 608 and internal imaging device 610 for alignment of those two datasets. As one non-limiting example, external imaging target 618 may be formed from particular materials, such that it is both visibly opaque to the visible light spectrum when depicted in camera imagery (e.g., ink, or any other optically visible material), as well as radiopaque, e.g., within x-ray imagery, MM imagery, CT scan imagery, or any other type of internal imaging data (e.g., metal, lead, etc.).

In some examples, external imaging target 618 may either be rigidly coupled to medical tool 602 (as described above), and/or may additionally include one or more EM sensors 604, so as to provide a dual reference point for alignment of the external imaging data (depicting at least a portion of the exterior of the patient's body 620) and for EM data of EM system 650 (describing the relative pose of medical tool 602 within the body of patient 620).

Similarly, in some examples, internal imaging target 628 may either be rigidly coupled to medical tool 602 (as described above), and/or may include one or more EM sensors 604, so as to provide a common reference point for both the internal imaging data (describing the interior anatomy of the patient's body 620) from internal imaging device 610, and for the EM data of EM system 650 (describing medical tool 602 within the interior anatomy of the patient's body 620).

In some examples in accordance with this disclosure, and as detailed further below with respect to FIG. 7, a single coherent object may include suitable physical and/or chemical properties such that the single object constitutes a "treble" common reference point, providing the functionality of all three of (1) an external imaging target 618 with respect to at least a portion of the exterior anatomy of patient 620; (2) an internal imaging target 628 with respect to the interior anatomy of patient 620; and (3) an EM reference point (with respect to medical tool 602 within patient 620). In such examples, the single coherent object provides a common location and orientation in space on which to base an alignment of corresponding coordinate systems for all three sets of data of system 100, e.g., to facilitate subsequent alignment by system 600 of (1) a virtual model 652 of medical tool 602 relative to a virtual model 654 of the internal anatomy of the body of patient 620; and (2) the virtual model 654 of the internal anatomy of the body of patient 620 relative to the exterior of the body of patient 620, either as viewed through a transparent display screen of HMD 108, or as depicted in 2-D imagery to be displayed on an opaque display screen of HMD 108.

Medical tool 602 includes electromagnetic (EM) sensor system 650, which in turn includes EM source 622 and at least one EM sensor 604. EM source 622 generates an EM field 624 (FIG. 6B). In some examples, but not all examples, EM source 622 may include a plurality of EM antennae, each EM antenna configured to emit an EM field defining a unique EM field pattern to be sensed (and distinguished) by EM sensor 604.

EM sensor 604 senses a strength (e.g., magnitude, phase, frequency, or the like) of the EM field at the location at which EM sensor 604 is positioned. EM sensor system 650 further includes communication circuitry (not shown) that receives (e.g., via a wired or wireless connection) signals generated by EM sensor(s) 604, and communicates the EM sensor signals to computing device 606 and/or HMD 108. Based on the sensed magnitude of the EM field at the location at which EM sensor 604 is positioned, computing device 606 may determine a distance and relative orientation between EM sensor 604 and EM source 622.

As depicted in the examples of FIGS. 6A and 6B, EM sensor 604 is located at a distal portion (e.g., at or near the tip) of flexible shaft 614 of medical tool 602. In the example of FIG. 6A, EM source 622 is located at base 616 of medical tool 602. Therefore, by determining a distance between EM sensor 604 and EM source 622, computing device 606 may determine a distance between the distal portion of flexible shaft 614 and base 616 of medical tool 602. By comparison, in the example of FIG. 6B, EM source 622 is located within a device that is physically distinct from medical tool 602.

In some examples, medical tool 602 may include more than one EM sensor 604. The use of a first EM sensor 604 in different orientation with respect to a second EM sensor 604 may provide additional information that computing device 606 may use to determine a 6-dimensional position of the distal portion of shaft 614 of medical tool 602 with respect to EM field generator 622. For example, medical tool 602 may include multiple EM sensors 604 clustered at a distal portion of medical tool 602 and/or distributed along flexible shaft 614. In some examples, medical tool 602 may include EM sensor(s) 604 near the distal tip of the tool, in addition to other types of sensors distributed along flexible shaft 614 (e.g., such as flex or strain sensors 104 of FIG. 1).

In some examples, the communication circuitry of EM sensor system 650 is located within base 616 of medical tool 602. The communication circuitry may be operatively connected to EM sensors 604, e.g., via a wired or wireless connection. In other examples, each of EM sensor(s) 604 includes respective local communication circuitry configured to transmit the respective EM sensor signals directly to computing device 606 and/or HMD 108.

Computing device 606 is an example of computing device 106 of FIG. 1 and includes one or more processors (e.g., "processing circuitry") and memory. In some examples, the processing circuitry of computing device 606 includes one or more microprocessors, digital signal processors (DSPs), application-specific integrated circuits (ASICs), field-programmable gate arrays (FPGAs), or any other equivalent integrated or discrete logic circuitry, as well as any combinations of such components. In some examples, the memory of computing device 606 includes random-access memory (RAM), read-only memory (ROM), programmable read-only memory (PROM), erasable programmable read-only memory (EPROM), electronically erasable programmable read-only memory (EEPROM), or flash memory, and includes executable instructions for causing the one or more processors to perform the actions attributed to them, as described herein. Further, this memory may be implemented entirely in hardware, software, or a combination thereof.

External imaging device 608 generates external image data depicting external imaging target 618 and, in some examples (but not all examples), at least a portion of the exterior of the patient's body 620. The external image data may further include one or more images of at least a portion of medical tool 602 within the 3-D environment (e.g., relative to the body of patient 620) or a distinct external imaging target 618. External imaging device 608 includes, as examples, a camera or a video-capture device. In some examples, external imaging device 608 is an example of imaging device 120 of FIG. 1. External imaging device 608 may additionally include an infrared-based imaging device, e.g., for infrared tracking of one or more groups of retroreflecting markers.

Internal imaging device 610 generates internal image data depicting at least a portion of an internal anatomy of the body of patient 620 and internal imaging target 628. Internal imaging device 610 includes, as examples, an x-ray fluoroscopy device, a magnetic resonance imaging (MM) device, a computed tomography (CT) scan device, an ultrasonic imaging device, or the like. In some examples, internal imaging device 610 is an example of imaging device 120 of FIG. 1.

As depicted in the examples of FIGS. 6A and 6B, system 600 includes head-mounted display (HMD) 108. In other examples, system 600 includes another type of display, such as a computer monitor, mobile device, tablet, laptop, television, transparent computer display, projector, a transparent display with a beamsplitter, or other type of screen-mounted display.

In accordance with techniques of this disclosure, EM system 650 transmits, to computing device 606, the values (e.g., EM sensor signals) sensed by EM sensor(s) 604 indicative of the magnitude of the EM field generated by EM source 622. Computing device 606 receives the plurality of values sensed by the EM sensor(s) 604 and determines, based on the EM field sensed by EM sensor(s) 604, a current "pose" or configuration of medical tool 602. For example, computing device 606 may determine, based on a magnitude of the EM field (as sensed by EM sensor 604 and as produced by EM source 622 located within base 616 of medical tool 602), a relative position of the distal portion of medical tool 602 with respect to base 616 of medical tool 102. While computing device 602 may use a single EM sensor 602 to determine the distance of the distal portion of medical tool 602 with respect to base 616, computing device 602 may use one or more EM sensors 604 to determine both a position and orientation (e.g., a pose) of the distal portion of medical tool 602 with respect to base 616.

Computing device 606 uses the information from EM sensor(s) 604 to create an altered digital structure representing medical tool 602. Computing device 606 may alter a digital replica or model of medical tool 602 to conform to the real-world physical structure of medical tool 602, such as based on the information provided by EM sensor(s) 604 located at least near a distal portion of flexible shaft 614. In some examples, responsive to determining a current pose of medical tool 602, computing device 606 generates (or adjusts) a 3-D model representation 652 of medical tool 602. For example, computing device 606 may translate, rotate, stretch, warp, bend, or otherwise modify a 3-D model representation 652 of medical tool 602 in order to approximate or match a real-world shape of medical tool 602 as determined by computing device 606 based on the signals generated by sensor(s) 604.

Computing device 606 receives, from internal imaging device 610, first (internal) image data depicting an internal anatomy of the body of the patient 620 and internal imaging target 628. Further, computing device 606 receives, from external imaging device 608, second (external) image data depicting external imaging target 618 and, in some cases, at least a portion of an exterior of the body of the patient 620.

Computing device 606 is further configured to determine, based on the signals indicative of the magnitude and direction (and/or phase, frequency, etc.) of the EM field, the first (internal) image data, and the second (external) image data, a relative alignment between the pose of the one or more EM sensors 604, a pose of the external imaging target 618, and/or a pose of the internal imaging target 628. For example, the components of imaging target 618 visible by external imaging device 608 and the components of imaging target 618 visible by internal imaging device 610 overlap one another. Further, EM source 622 of base 616 may overlap imaging target 618. In other examples, the components of imaging target 618 visible by external imaging device 608, the components of imaging target 618 visible by internal imaging device 610, and EM source 622 are positioned a negligible distance from one another or are positioned a predetermined distance from one another. Because imaging target 618 and EM source 622 are a known distance (e.g., zero or a predetermined distance) from one another, computing device 606 may align information captured by EM sensor system 650, external imaging device 608, and internal imaging device 610 with respect to one another to generate XR content as described in more detail below.

When determining the relative alignments between the EM sensor system 650, the internal imaging system (e.g., internal anatomy and internal imaging target 628), and the external imaging system (e.g., external imaging target 618), computing system 606 may be configured to determine a first pairwise alignment between any two of these three systems, a second pairwise alignment between any other two of these three systems, and in some examples, combine the two pairwise alignments to determine a common "global" relative alignment or coordinate system.

For instance, in a first example, computing device 606 is configured to determine the global relative alignment by determining a first relative alignment between the pose of the one or more EM sensors 604 (e.g., a pose of EM sensor(s) 604 with respect to an EM coordinate system) and a pose of the internal imaging target 628 (e.g., a pose of target 628 relative to an internal imaging coordinate system). In some such examples, computing system 606 is configured to generate, based on the adjusted 3-D model representation 652 of the medical tool 602 and the first relative alignment between the pose of the one or more EM sensors 604 and the pose of the internal imaging target 628, the visual representation 652 of the medical tool 602 within the internal anatomy 654 of the patient 620. For instance, determining the "first" relative alignment may include determining, based on a predefined distance between the EM sensor system and the internal imaging target 628, the pose of the one or more EM sensors 604 with respect the internal imaging coordinate system, and/or the pose of the internal imaging target 628 with respect the EM coordinate system.

In some examples, computing system 606 is the further configured to determine a "second" relative alignment, such as between the pose of external imaging target 618 and the pose of internal imaging target 628. For instance, computing device 606 may be configured to determine the "second" relative alignment between the pose of the external imaging target 618 and the pose of the internal imaging target 628 by determining, based on a predefined distance between the internal imaging target 628 and the external imaging target 618, the pose of the internal imaging target 628 with respect the external coordinate system, or equivalently, the pose of the external imaging target 618 with respect to the internal coordinate system.

Computing device 606 uses the adjusted 3-D model representation 652 of medical tool 602, the external imagery from external imaging device 608 depicting medical tool 602, and the internal images of medical tool 602 from internal imaging device 610 to generate XR content 612, including a visual representation 652 of medical tool 602 with respect to a visual representation 654 of the internal anatomy of patient 620, and further, with respect to an exterior, 3-D environment. For example, in cases in which an intended output device includes a transparent display screen (e.g., a transparent visor of HMD 108), computing device 606 uses images depicting external imaging target 618 positioned on medical tool 602 as a reference point to localize a position and/or orientation (e.g., a pose) of medical tool 602 within a 3-D, real-world environment with respect to patient 620. Further, computing device 606 uses images depicting internal imaging target 628 positioned on medical tool 602 as a reference point to localize a position and/or orientation of medical tool 602 within the 3-D, internal anatomy image data of patient 620.

For instance, computing device 606 may use the received signals from EM sensor 604 to determine the pose of medical tool 602 and generate a representation of medical tool 602 in the determined pose, as described above. Further, computing device 606 renders, based on the determined relative alignment, the representation of medical tool 602 positioned within a visual representation of the internal anatomy of the body of patient 620. Computing device 606 outputs, based on the determined relative alignment, the representation 652 of medical tool 602 and the visual representation 654 of the internal anatomy of the body of patient 620 onto the transparent display screen of HMD 108 at a position that, from the perspective of the user 110, is "overtop" of the real-time position of the body of the patient 620 in order to simulate a "transparent" view of an accurate position and orientation of tool 602 through the body of the patient 620. Computing device 606 may further incorporate motion-sensor data from an inertial measurement device (IMD), such as an accelerometer, incorporated within HMD 108 in order to continuously "update" the position and orientation of the XR content 612 on the transparent display screen to "register" or "fix" the XR content in place from the perspective of user 110 during a movement of HMD 108 (e.g., as user 110 moves his or her head).

In other examples in which an intended output device does not include a transparent display screen (e.g., an LCD or other display screen of a computing device, such as a mobile device, VR headset, or the like), the XR content generated by computing device 606 may include a composite image of the visual representation 652 of the medical tool 602 within the internal anatomy 654 overlaid upon a portion of the exterior of the body of the patient 620, e.g., as depicted within the second (external) image data or other image data depicting a current position and orientation of the patient's body. For instance, computing device 606 uses the received signals from EM sensor 604 to determine the pose of medical tool 602 and generate a representation 652 of medical tool 602 in the determined pose, as described above. Further, computing device 606 renders, based on the determined relative alignment, the representation 652 of medical tool 602 positioned within a visual representation 654 of the internal anatomy of the body of patient 620. Computing device 606 overlays, based on the determined relative alignment, the representation 652 of medical tool 602 and the visual representation 654 of the internal anatomy of patient 620 over a visual representation of the exterior of the body of patient 620. Computing device 606 outputs the XR content 612 for display on an XR device (e.g., HMD 108) for display to user 110.

As depicted in the example of FIG. 6A, XR content 612 may include a visual representation 652 of medical tool 602 (e.g., the adjusted 3-D model representation of medical tool 602) positioned within a visual representation 654 of the internal anatomy of the body of the patient 620. Further, XR content 612 may depict a visual representation 652 of medical tool 602 and visual representation 654 of the internal anatomy of the body of the patient 620 overlaid upon a visual representation of the real-world environment (e.g., depicting at least a portion of the exterior of the body of patient 620), so as to present a simulated "transparent view" representing a real-world position and orientation of medical tool 602 within the internal anatomy of the patient 620 (e.g., relative to one or more simulated internal organs of the patient), and relative to the real-world position and orientation of the exterior of the body of patient 620. In some examples, system 600 may include multiple display devices and/or HMDs 108 that enable multiple users 110 to visualize medical tool 602 within the internal anatomy of patient 620 and within the 3-D real-world environment from the perspective of each user 110.

FIG. 6B is a conceptual diagram illustrating a portion of XR system 600 of FIG. 6A in further detail. In particular, FIG. 6B illustrates an example of EM sensor system 650 that includes one or more EM sensors 604 coupled to flexible medical tool 602 of system 600. As shown in the example of FIG. 6B, EM sensor(s) 604 are configured to sense a plurality of signals indicative of a magnitude and direction (and/or phase, frequency, etc.) of EM field 624 generated by EM source 622 of EM sensor system 650. For example, as detailed further below, one or more EM sensor(s) 604 are configured to sense a magnitude and direction of EM field 624, from which computing device 606 of FIG. 6 may determine a pose (e.g., relative position and orientation) of EM sensor 604 relative to EM source 622.

In the example of FIG. 6B, medical tool 602 includes a Transjugular Intrahepatic Portosystemic Shunt (TIPS) set that incorporates a modified sheath or needle outfitted with or more electromagnetic (EM) position sensors 604. An EM field generator or EM source 622 is located near patient 620 and generates one or more field patterns 624 that are sensed by EM position sensor(s) 604. Each EM position sensor(s) 604 generates a signal indicative of a position of the EM sensor 104 relative to EM field generator 622 and outputs the signal to an XR system, such as to computing device 606 and/or HMD 108.

EM field source 622 includes circuitry configured to generate a controlled electromagnetic field 624 having known or controllable parameters (e.g., magnitude, direction, and/or other EM characteristics) configured to be detected by EM sensor(s) 604. In some cases, such as the example shown in FIG. 6A, EM field source 622 is integrated into a base 616 of medical device 602. In other examples, such as the example depicted in FIG. 6B, EM field source 622 is depicted as being physically distinct from medical tool 602. In some examples, EM position sensors 604 determine their position and orientation relative to EM field generator 622.

In some examples in accordance with this disclosure, computing device 606 is configured to receive, from one or more EM sensors 604 of EM sensor system 650, signals indicative of a magnitude of an EM field 624 generated by an EM source 622 of the EM sensor system 650, wherein the one or more EM sensors 704 are disposed at a distal portion of a flexible shaft 614 of medical tool 602 configured for insertion into a body of patient 620. Computing device 606 and/or another XR system (e.g., HMD 108) may then determine, based on the signals indicative of the magnitude of the EM field, a pose of the one or more EM sensors 604 and adjust, based on the determined pose of the one or more EM sensors 604, a three-dimensional (3-D) model representation 652 of the medical tool.

External imaging target 618 and internal imaging target 628 may be attached to EM field generator 622. In some examples, external imaging target 618 and internal imaging target 628 are the same imaging target. In some examples, either the internal target, the external target, or both targets have respective EM sensors 604. Imaging targets 618, 628 provide an imaging marker for an augmented reality (AR) or extended reality (XR) HMD 108, and associated software, to align data from EM system 650, internal image data obtained from internal imaging device 610 (of FIG. 6A) and exterior image data obtained from external imaging device 608 (of FIG. 6A) to one another.

When the relative position between the perspective of HMD user 110 and EM position trackers 604 is known, XR software of computing device 606 creates a visual overlay 612 of the operative tools even when occluded by tissue of the body of patient 620. This allows the user to continuously visualize the position and orientation of the TIPS needle and sheath 602.

As described above, imaging targets 618, 628 each include a visually distinct marker that, when depicted within imagery captured by, e.g., external imaging device 608 and/or internal imaging device 610, computing device 606 can detect the imaging targets 618, 628 within the imagery, such as by using pattern-recognition algorithms. In some examples, imaging targets 618, 628 are rigidly coupled to EM field source 622 such that a distance and orientation between imaging targets 618, 628 and EM field source 622 is known. By extension, computing device 606 may determine a pose of EM sensor(s) 604 (relative to external imaging target 618) based on received EM sensor data indicating the pose of EM sensor(s) 604 relative to EM field source 622. In some cases, system 600 may include a modular mounting system which mechanically registers to both the EM field generator 622 and imaging targets 618, 628. This mounting system may be substantially rigid such that, when the EM field generator 622 and/or imaging targets 618, 628 are installed, their relative poses are known.

In some examples, external imaging target 618 includes an object including three or more elongated arms, each arm having a different length and oriented at a known angle (e.g., about 90 degrees) with respect to the other arms so as to define an unambiguous orientation of external imaging target 618 when observed within external imagery from external imaging device 608 (e.g., a camera). Similarly, each EM sensor 604 may include two or more individual EM sensor units oriented at a known angle (e.g., about 90 degrees) with respect to each other so as to define an unambiguous orientation of the respective EM sensor 604, as indicated by, and as determinable from, the collected EM sensor signals.

As described above, in some examples, interior imaging target 628 is fixed at a predetermined position relative to a position of the EM sensor system 650 (e.g., rigidly coupled to EM source 622). Similarly, exterior imaging target 618 may be fixed at a predetermined position relative to the position of the interior imaging target 628, such that the relative alignments between the various coordinate systems are known or readily determinable. In some examples, positions of any or all of EM source 622, interior imaging target 628, and/or exterior imaging target 618 may all be mutually fixed with respect to a rigid portion of the body of patient 620 that is discernable both from external imagery (e.g., visible or determinable through the patient's skin) as well as within the internal imagery. For instance, a rigid portion of the body of patient 620 may include a bony anatomy of the patient, such as the patient's skull or other similar body part. In some such examples, computing system 606 is configured to determine the relative alignment(s) between the datasets based at least in part on known distances of the interior imaging target 628 and the exterior imaging target 618 from the rigid portion of the body of patient 620. In some such examples, computing system 606 is configured to "register" the bony anatomy of the body of patient 620 to interior imaging target 628, exterior imaging target 618, and/or EM sensor(s) 604. As one particular example of the registration process, EM sensor(s) 604 may be moved or "swiped" along the rigid portion of the patient's body while monitoring the sensed EM signals, such that the location of the rigid portion of the patient's body relative to EM source 622 is known, and by extension (from internal and external imagery of the rigid anatomy portion), the location of EM source 622 relative to the internal coordinate system and/or the external coordinate system.

In some examples, internal imaging target 628 includes an asymmetrical marker (e.g., an object) formed from a visually contrasting material (e.g., a radiopaque material or the like) such that it is discernable within internal imaging data, such as CT scan imagery, MRI imagery, fluoroscopic imagery, ultrasonic imagery, or the like. In some examples, internal imaging target 628 may have a geometric shape that is substantially asymmetrical, such that its orientation is unambiguous when located within the internal imaging data. In some examples, internal imaging target 628 includes an object having at least four points of reference, each point of reference made from a material having a different relative density (measured in "Hounsfield" units) such that the points of reference define an unambiguous six-degrees-of-freedom (6DOF) orientation of internal imaging target 628 in 3-D space. As used herein, "6DOF" refers to three position dimensions (e.g., up/down; left/right; forward/back) and three axes of rotational motion (e.g., yaw; pitch; roll). In some such examples, the Hounsfield density of each point of reference may be substantially greater than a Hounsfield density of the body of the patient 620, so as to easily distinguish the points of reference within the internal imagery. Additionally or alternatively, internal imaging target 628 may include an object having at least four points of reference (e.g., the same four points or an additional four points), wherein each point of reference defines a different geometric shape so as to define an unambiguous 6DOF orientation of internal imaging target 628 in 3-D space. Additionally or alternatively, internal imaging target 628 may include an object having at least four points of reference (e.g., the same four points or an additional four points), wherein each pair of distance between any two points is unique to the other pairwise distances as to define an unambiguous 6DOF orientation of internal imaging target 628 in 3-D space.

In some examples, internal imaging target 628 is affixed to a mounting system at a first position, and external imaging target 618 is affixed to the mounting system at a second position that is a predetermined distance from the first position, such that the relative alignment between the internal and external coordinate systems are known. For instance, the mounting system may be rigidly mounted to a bed on which patient 620 lies while the internal imaging data is collected. In some such examples (but not all such examples), the mounting system may include a robotic C-arm, wherein internal imaging target 628 includes a plurality of radiopaque markers affixed to the robotic C-arm, and wherein external imaging target 618 includes a geometric shape that has an unambiguously determinable orientation in 3-D space. Additionally or alternatively, one or more components of EM sensor system 650 may be affixed to the mounting system at a third position that is a predetermined distance from the first position and/or the second position.

In some examples, a camera (e.g., external imaging device 608) on HMD 108 detects external imaging target 618 and determines a location and orientation in space of external imaging target 618 relative to HMD 108, and by extension, the perspective of the XR user 110. Similarly, HMD 108 may receive internal imaging data from, e.g., an MRI imaging device or a CT scanning device and determine a location and orientation in space of internal imaging target 628 within the internal imaging data relative to HMD 108 and the perspective of the XR user 110. HMD 108 may also use imaging targets 618, 628 to align a determined pose of a virtual representation of medical tool 602 to external imaging data and internal imaging data.

In some examples, HMD 108 determines the relative position and orientation of the EM field generator 622 using the camera 608 mounted on HMD 108. The EM positioning system 650 and imaging target system 618 thus output a pair of relative coordinate transformations. When combined, the relative position and orientation between the perspective of HMD user 110 and the EM position trackers 604 can be calculated (e.g., by computing device 606, which may be integrated within HMD 108). In some examples herein, additional visual overlays can be provided to help guide a medical procedure involving medical tool 602 (e.g., a TIPS procedure) for patient 620. In some instances, system 600 includes an internal imaging device 610 configured to capture internal image data depicting an internal anatomy of patient 620. In one illustrative, non-limiting example, patient 620 may undergo a CT scan prior to a TIPS procedure. In some such examples, the anatomy around the liver of patient 620 can be segmented to create a digital, 3-D geometric model 654 of the patient's internal anatomy, which can be overlayed onto real-time imagery (e.g., from external imaging device 608) during the TIPS procedure, in order to produce a simulated "transparent" view of the patient's body. In one particular example, computing device 606 may use internal imagery (e.g., CT scan imagery) from internal imaging device 610 to segment the blood vessels of the patient's liver, in order to help guide the TIPS needle and sheath 602 from, for example, the inferior vena cava (IVC) and hepatic veins into the portal vein.

In some examples in which system 600 uses internal imaging data (e.g., from a CT scan) in an overlay during an AR-TIPS procedure, computing device 606 is further configured to determine the position and orientation (e.g., a relative alignment) of the digital, 3-D internal imaging data from the perspective of the user 110 of HMD 108. As one such example, an external imaging target 628 may be placed outside of the body of patient 620, and may be used by computing device 606 to perform this additional coordinate transformation or relative-alignment determination.

In some cases, internal imaging target 628 may include one or more particular physical parameters so as to define, and readily indicate, an unambiguous pose of external imaging target 628, both within internal imaging data (e.g., CT scans) and within external imaging data (e.g., visual imagery captured by camera 608). For instance, the geometry of internal imaging target 628 may be designed such that its position and orientation can be determined unambiguously from internal imaging data (e.g. from Digital Imaging and Communications in Medicine (DICOM) volumetric-pixel (or "voxel") computed tomography (CT) scan data). The physical composition of internal imaging target 628 may be selected such that the target 628 can be scanned with a CT scanner, or other similar internal imaging device 610, with good contrast. Internal imaging target 628 may include individual components that each have a well-defined attenuation (e.g. a narrow range of Hounsfield units). A well-defined attenuation (e.g., a material having a Hounsfield unit value sufficiently greater than the surrounding tissue of the patient) can help computing device 606 to locate internal imaging target 628 within internal imaging data (e.g., 3-D voxel data) by filtering out all voxels outside of a particular range of attenuations.

In some examples herein, internal imaging target 628 may be fixed in place relative to patient 628 and scanned, along with the patient 620, by internal imaging device 610. During anatomy segmentation, a position of the anatomy relative to internal imaging target 628 is known. During a subsequent TIPS procedure, the position of internal imaging target 628 may be registered to the external imaging device (camera) 608, and/or the EM position-tracking system 650. In some cases, the internal imaging target 628 is distinct from external imaging target 618. In other cases, internal imaging target 628 includes an affixed EM position tracker. Finally, internal imaging target 628 may have mechanical features which can "interlock" with EM field generator 622 in only one configuration (e.g., one unambiguous pose). When EM field generator 622 and internal imaging target 628 are interlocked in this way, the position of each, relative to the other, is known. In some cases, EM field generator 622 may itself function as internal imaging target 628. That is, EM field generator 622 may be scanned, by internal imaging device 610, along with patient 620 such that their relative poses are known.

In some examples, computing system 606 is configured to determine a pose of medical tool 602 relative to the internal anatomy of patient 620 based on a previous trajectory of medical tool 602, as indicated by the signals indicative of the magnitude of the EM field received from EM sensor(s) 604. For example, computing system 606 may be configured to determine and monitor a path of motion of EM sensor(s) 604 and compare a geometric shape (e.g., a curvature) of the path of motion to a geometric shape within the internal anatomy of the patient. In other words, computing system 606 may attempt to "match" the trajectory of EM sensor(s) 604 to a particular lumen, such as the interior of a vessel or vein of patient 620 (as depicted within internal imaging data), in order to "locate" EM sensor(s) 604 within the patient's body. In some such examples, computing system 606 may be configured to generate XR content 612, such as a simulation of medical tool 602 at a particular location and/or trajectory within the internal anatomy of patient 620, overlaid upon a corresponding portion of the exterior of the body of patient 620 depicted within the second (external) image data. In some examples, the computing system 606 may improve the registration between the real anatomy of a patient and the analogous virtual anatomy 654 using an algorithm which minimizes the distances between the interior space of the virtual anatomy 654 and the path of motion of the EM sensor(s) 604 over time.

For instance, computing device 606 may use the path of motion of the EM sensors 604, constrained by, for example, known positions of vessel walls of the patient's vasculature, to refine the alignment between real and virtual anatomy of patient 620. In some such examples, computing device 606 may be configured to substitute this path-of-motion tracking for determining a relative alignment based on an internal imaging target 628. As one example, computing device 606 may filter out "anomalous" or outside-threshold datapoints recorded by EM sensors 604, such as datapoints with random artifacts, datapoints indicating that a rate of motion of the sensor was outside an expected range, datapoints indicating that a distance between two sensors was outside an expected range, or the like. Computing device 606 may then filter out additional datapoints indicating a position of sensor 604 that is outside an expected vein or vessel geometry, reduce or minimize a positive-signed distance of the motion path points outside of an expected vein geometry (e.g., only add up positive distances outside veins, ignore negative distances inside veins), and/or reduce or minimize the distance between the datapoints and a central longitudinal axis of an expected vein geometry, in order to determine a relative alignment between EM sensors 604 and the internal anatomy of patient 620.

Figure 7A:
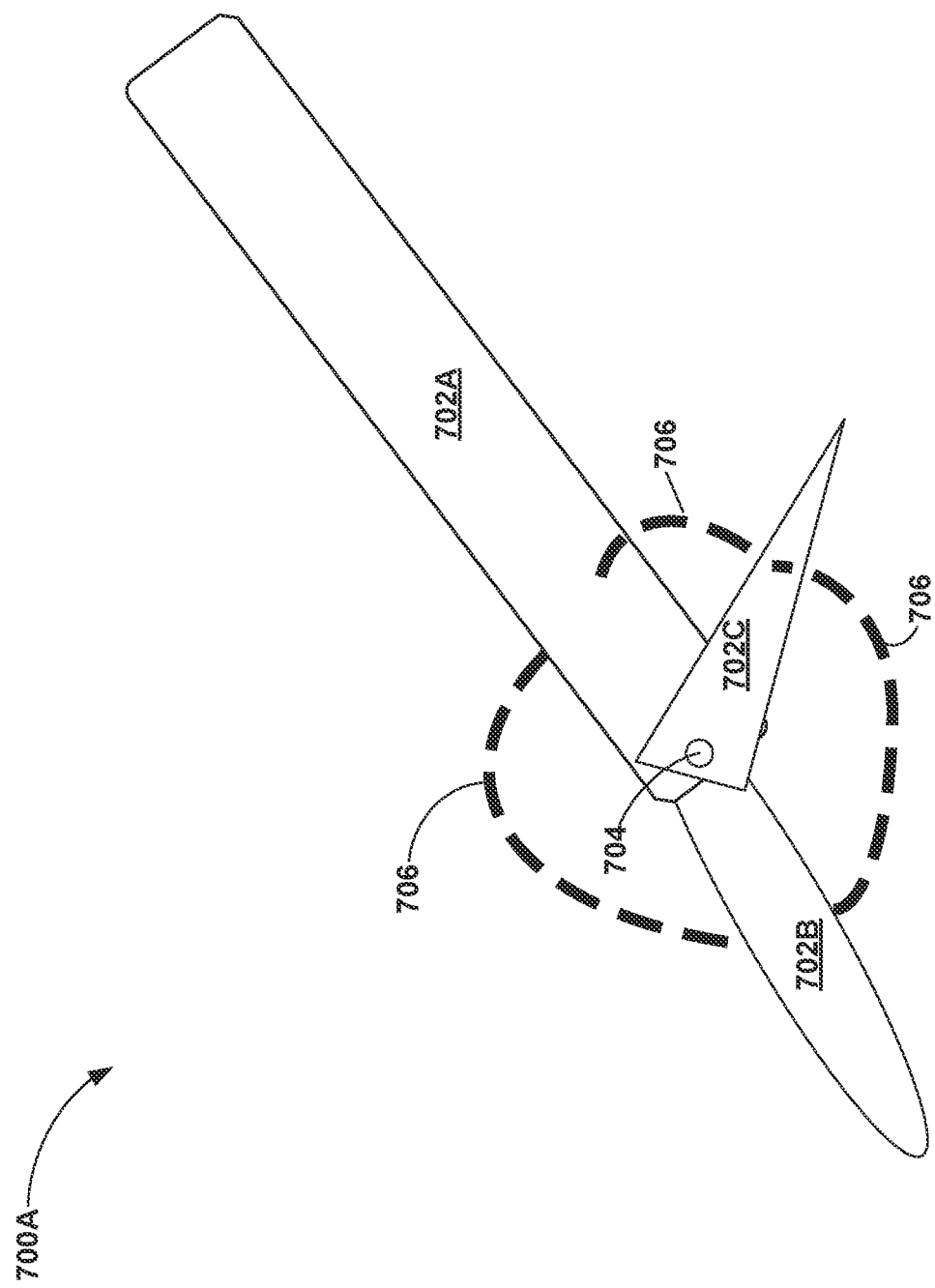
FIGS. 7A-7C is a conceptual diagram illustrating examples of multi-functional fiducial markers.
Figure 7B:
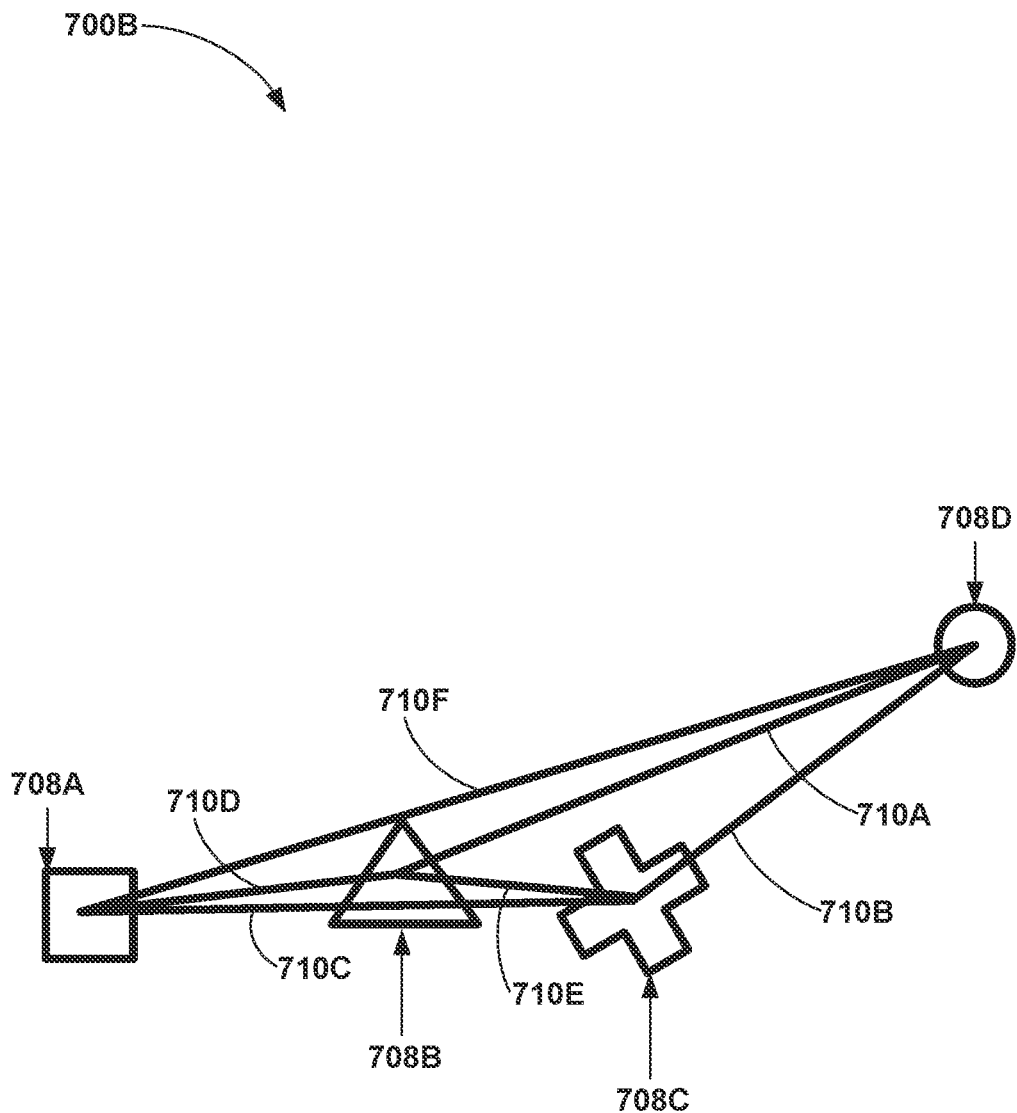
Figure 7C:
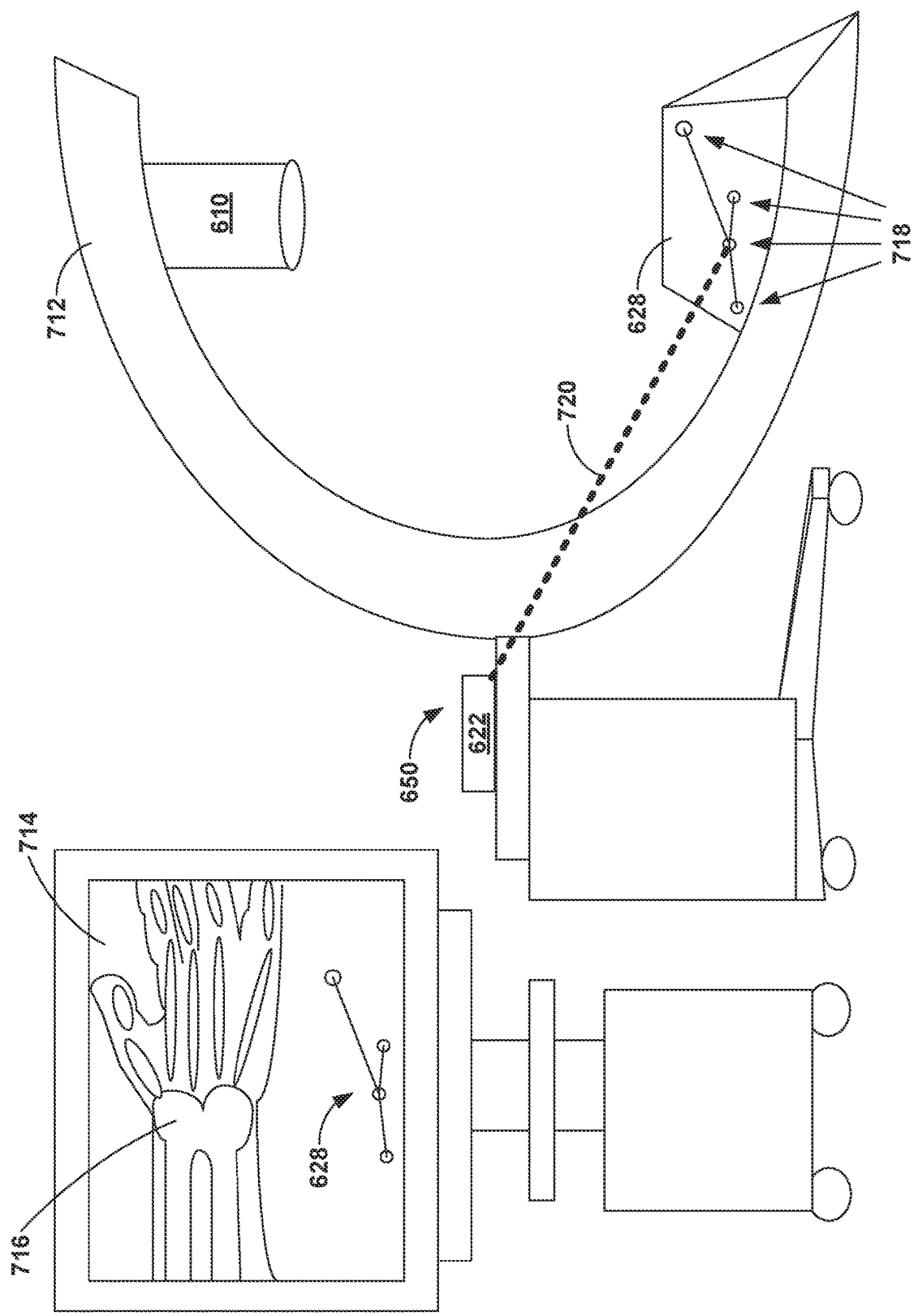

FIGS. 7A-7C illustrate various examples of multi-functional fiducial markers for aligning two or more distinct types of datasets, as described above. For instance, FIG. 7A is a conceptual diagram illustrating an example fiducial marker 700A, which may be a 2-D marker (e.g., an image printed on a surface) or a physical, 3-D object. Fiducial marker 700A includes at least three elongated arms 702A-702C (collectively, "arms 702," or in the alternative, "arm 702") extending radially outward from a common center point 704. As shown in FIG. 7A, each arm 702 extends a different distance away from center point 704 (e.g., defines a different length), and is oriented at a different angle 706 with respect to the other two arms. In this way, fiducial marker 700A defines a single, unambiguously determinable orientation (e.g., having six-degrees-of-freedom (6DOF)), in 3-D space. Accordingly, fiducial marker 700A may be used at least as an external imaging target 618.

In examples in which fiducial marker 700A is formed from a radiopaque material, fiducial marker 700A may additionally be used as an internal imaging target 628, thereby providing "dual" reference-point functionality. In examples in which fiducial marker 700A has a fixed, known, or readily determinable pose relative to medical tool 602, and/or wherein any of arms 702 include embedded EM sensors 604, fiducial marker 700A may additionally be used as an EM reference point for EM system 650, thereby providing "treble" reference-point functionality.

As further shown in FIG. 7A, arms 702A-702C may be formed to have substantially different shapes (e.g., rectangular, rounded, and triangular shapes, respectively). Such configurations which may further help image-processing software (e.g., pattern recognition) of computing device 606 to more quickly and/or more easily distinguish the orientation of fiducial marker 700A, particularly when depicted at an oblique orientation within a 2-D dataset (e.g., internal or external image data) that either obscures one of the arms 702 or distorts the "apparent" lengths of arms 702 and/or the angles 706 therebetween.

FIG. 7B is a conceptual diagram illustrating another fiducial marker 700B that includes at least four points of reference 708. Each point of reference defines a different geometric shape such the four points of reference 708 define an unambiguously determinable six-degrees-of-freedom (6DOF) orientation of the internal imaging target in three-dimensional (3-D) space when captured in external imaging data. In examples in which the points of reference 708 are at least partially radiopaque, fiducial marker 700B may constitute a dual external-and-internal imaging target 618/628.

Additionally or alternatively, at least two of reference points 708 (e.g., points 708B, 708D) of fiducial marker 700B define a separation distance 710A that is unique from at least five other separation distances 710B-710F (e.g., between all other pairwise distances between any other pair of reference points 708), such the at least four points of reference 708 define an unambiguously determinable six-degrees-of-freedom (6DOF) orientation of the internal imaging target in three-dimensional (3-D) space.

FIG. 7C is a conceptual diagram illustrating an example mounting system for various fiducial markers such that the relative poses (e.g., distances and orientations) between the markers are fixed and known, and accordingly, that the respective datasets may be easily aligned. In the example shown in 7C, the mounting system is depicted as a robotic C-arm 712, such as for an X-ray machine. In such examples, the X-ray machine may constitute the internal imaging device 610, configured to capture internal imaging data 714 depicting an internal anatomy 716 of a patient 620 (FIG. 6A).

As shown in FIG. 7C, the fiducial-marker-mounting system includes an internal imaging target 628 in the form of a plurality of radiopaque markers 718 affixed to the robotic C-arm 712 such that the position and orientation of the imaging target 628 is known. In some such examples, internal imaging target 628 comprises an object having at least four points of reference (e.g., each radiopaque marker 718), each point of reference comprising a different degree of radiopacity, or "Hounsfield" density, such that the four points of reference 718 collectively define an unambiguously determinable six-degrees-of-freedom (6DOF) orientation of the internal imaging target 628.

Additionally or alternatively, EM sensor system 650 (e.g., including at least EM generator 622) is rigidly coupled to the mounting system 712 at a position that is a known or predetermined distance 720 from the internal imaging target 628. Additionally or alternatively, an external imaging target may be rigidly coupled to the mounting system at a known or predetermined distance from either of internal imaging target 628 or EM system 650. In the example depicted in FIG. 7C, the internal imaging target 628 may likewise function as an external imaging target, in that the radiopaque markers 718 are in an asymmetrical arrangement defining an orientation is unambiguously determinable within external imaging data.

Figure 8A:
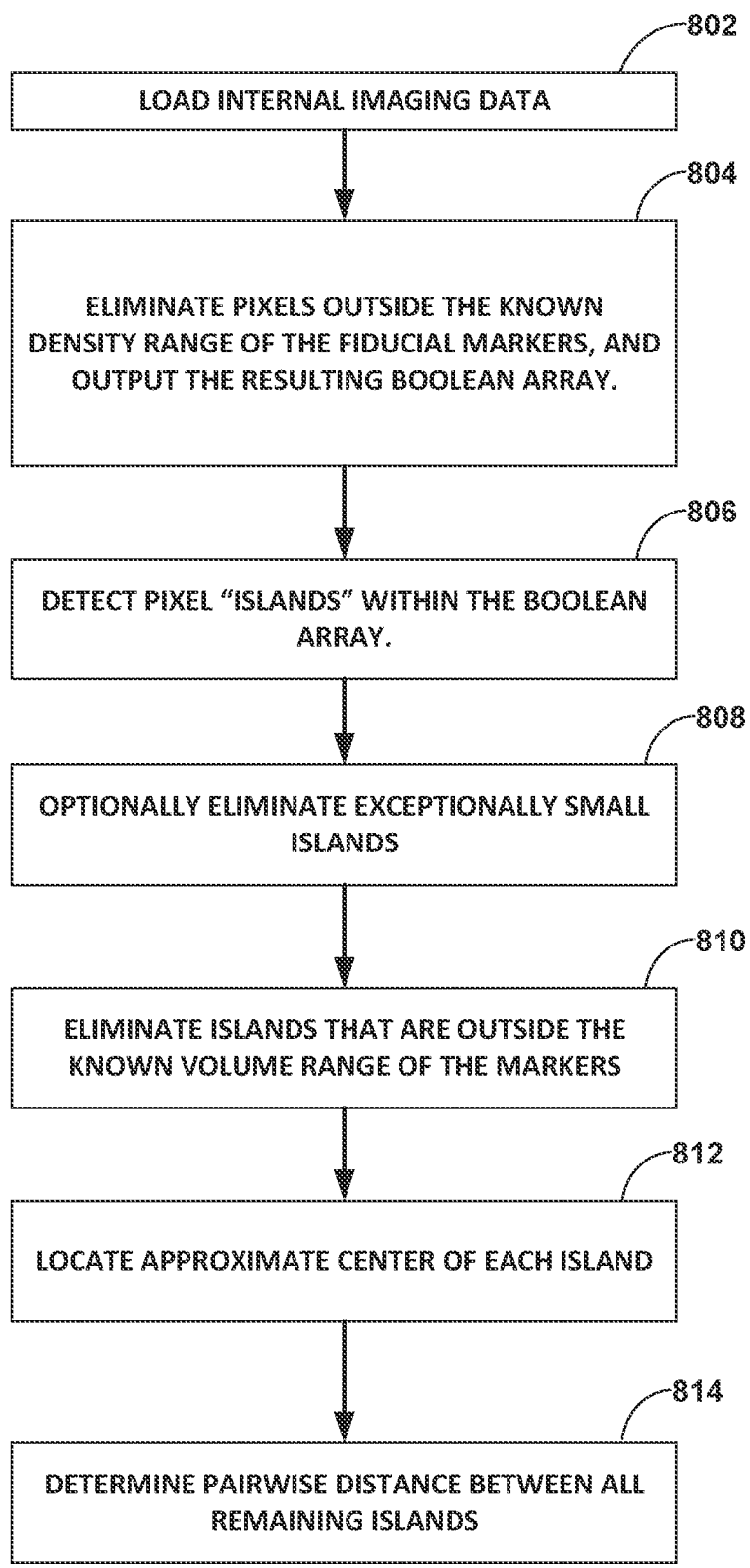
FIGS. 8A and 8B are flowcharts illustrating example techniques for determining a relative alignment for an array of fiducial markers.

FIG. 8A is a flowchart illustrating an example technique for determining a "rough" or approximate alignment (e.g., respective relative positions and orientations) of an array of fiducial markers 928 having known sizes and densities. Fiducial markers 928 are examples of internal imaging target(s) 628 of FIGS. 6A and 6B. The alignment techniques of FIG. 8A may be performed, for example, by computing device 606 of FIG. 6A, and are described for purposes of illustration with respect to the two-dimensional (2-D) pixel arrays depicted in FIGS. 9A-9D. However, the techniques of FIG. 8A apply similarly to three-dimensional (3-D) voxel arrays, mutatis mutandis (e.g., by substituting "area" with "volume," etc.).

After a patient standard has been imaged (e.g., CT-scanned, MRI-scanned, etc.), a computing system 606 (FIG. 6) loads the resulting internal imaging data 902A (FIG. 9A), such as Digital Imaging and COmmunications in Medicine (DICOM) data (802). The internal imaging data 902A includes a 2-D array of pixels (or a 3-D array of voxels, as appropriate), some of which represent the scanned internal imaging targets 928, and others of which represent random noise in the internal imaging data file.

Computing system 606 applies a density filter to the internal image data 902A. For instance, the relative color (e.g., relative darkness) of each pixel corresponds to the relative density of the respective object imaged at that pixel's location. Accordingly, computing system 606 scans through each pixel of internal imagery 902A and compares the color of that pixel to a range of "permissible" colors corresponding to the known densities of the fiducial markers 928 (e.g., measured in Hounsfield units). In other words, computing system 606 assigns to each pixel a Boolean value ("YES" or "NO") indicating whether the color of the pixel falls within the expected density range for the fiducial markers 928 (e.g., shown in white in FIG. 9B), or whether the color of the pixel does not fall within the expected density range for the fiducial markers 928 (e.g., shown in black in FIG. 9B). Computing system 606 then outputs the resulting Boolean array 902B shown in FIG. 9B. In this way, computing system 606 effectively eliminates all pixels that fall outside the expected color/density range (shown in black in FIG. 9B), and assimilates all pixels that fall within the expected color/density range to a common color (e.g., white) (804).

Computing system 606 then scans the Boolean array 902B and identifies all "islands," or groups 904 of adjacent white pixels that are completely surrounded by black pixels (or vice versa, as appropriate). In some instances, such as when the Boolean array 902B includes a large number of single-pixel islands 904, subsequent image-processing by computing system 606 may become very slow. In some such instances, computing system 606 may be optionally configured to eliminate "exceptionally" small pixel islands 904, or in other words, to "de-speckle" the Boolean array 902B. For instance, computing system 606 may be configured to first apply an "erode" filter to reduce the size of all pixel islands by a predetermined proportion, thereby "shrinking" all of the below-threshold-size pixel islands out of existence, and then to apply a "dilate" filter to re-expand all remaining pixel islands 904 back to their original size (808).

After applying the density-based pixel filter, computing system 606 applies a size-based filter. For instance, computing system 606 may measure the area (or volume, as appropriate) of each pixel island 904 and determines whether the island 904 falls within an expected size range associated with the known sizes of the fiducial markers 928. As shown in FIG. 9C, computing system 606 then "eliminates" all pixel islands 904 of pixels that fall outside the expected size range, e.g., that are either too large or too small to be indicative of the position of a fiducial marker 928 (810).

At this stage, the only remaining pixel islands 904 should indicate the positions of the fiducial markers 928 (e.g., four pixel islands 904, in the example shown in FIG. 9C). As shown in FIG. 9D, computing system 606 may then determine the approximate center 906 of each pixel island (812), and then measure the pairwise distance 908 (e.g., distances 710 of FIG. 7B) between the centers 906 of the remaining pixel islands (six pairwise distances 908, in the example shown in FIG. 9D), in order to determine the approximate relative alignment between the fiducial markers 928 (814).

Figure 8B:
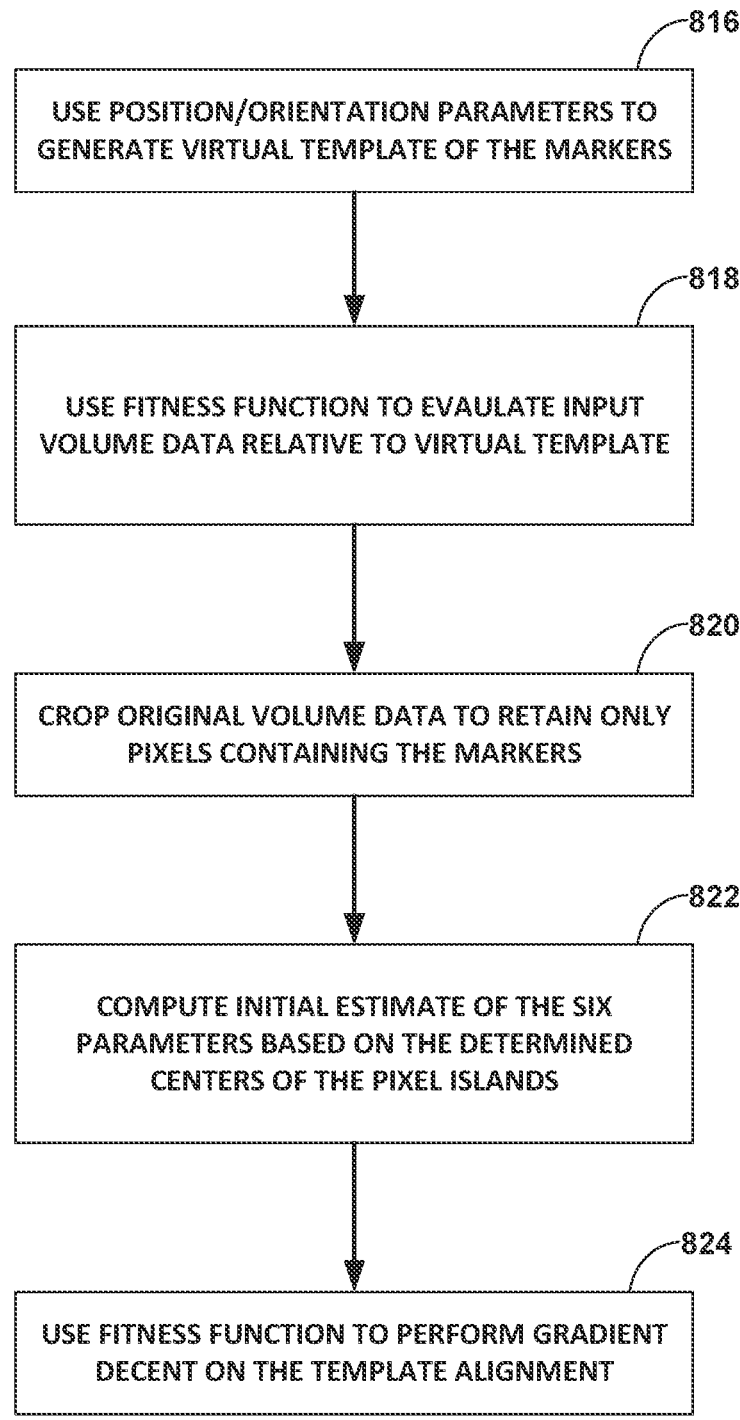

FIG. 8B is a flowchart illustrating a technique for determining a precise (e.g., sub-pixel-level) relative alignment for the array of fiducial markers 928 of FIG. 9A. For instance, the precise-alignment techniques of FIG. 8B may be performed by computing system 606 of FIG. 6A after one or more rough or approximate alignment techniques (e.g., the techniques of FIG. 8A) have been performed for the array of fiducial markers 928.

Computing system 606 generates a first function or algorithm configured to receive (e.g., as user input) a set of input parameters and create, based on the parameters, a virtual template of the array of fiducial markers 928 (816). For instance, the function may be configured to receive three "position" input parameters (x, y, z) and three "orientation" input parameters (yaw, pitch, roll). The subsequently generated virtual template may include virtual representations of the fiducial markers 928, each virtual marker having a radiodensity equal to the average value of the known radiodensities of the physical fiducial markers 928.

Computing system 606 applies a second function or algorithm configured to evaluate (e.g., determine and indicate) how well the virtual template, at a particular position and orientation, matches some input volume data (818). For instance, computing system 606 may apply a cross-correlation function or other similar function to the virtual template for the given position and orientation.

Computing system 606 then crops the original volume data from the DICOM data 902A (FIG. 9A) to retain only the pixels (or voxels, as appropriate) representing the fiducial markers 928 (820). Using the cropped DICOM data, computing system 606 computes an initial "guess" of the virtual template parameters (822), e.g., based on the determined relative positions of the centers 906 of the pixel islands 904, as described above with respect to FIG. 8A.

Computing system 606 then applies the fitness function to perform gradient descent on the template alignment (824) to precisely determine the relative alignment of the fiducial markers 928, e.g., up to a resolution that is higher than the resolution of the pixels of the DICOM data 902A, in some instances.

Figure 10:
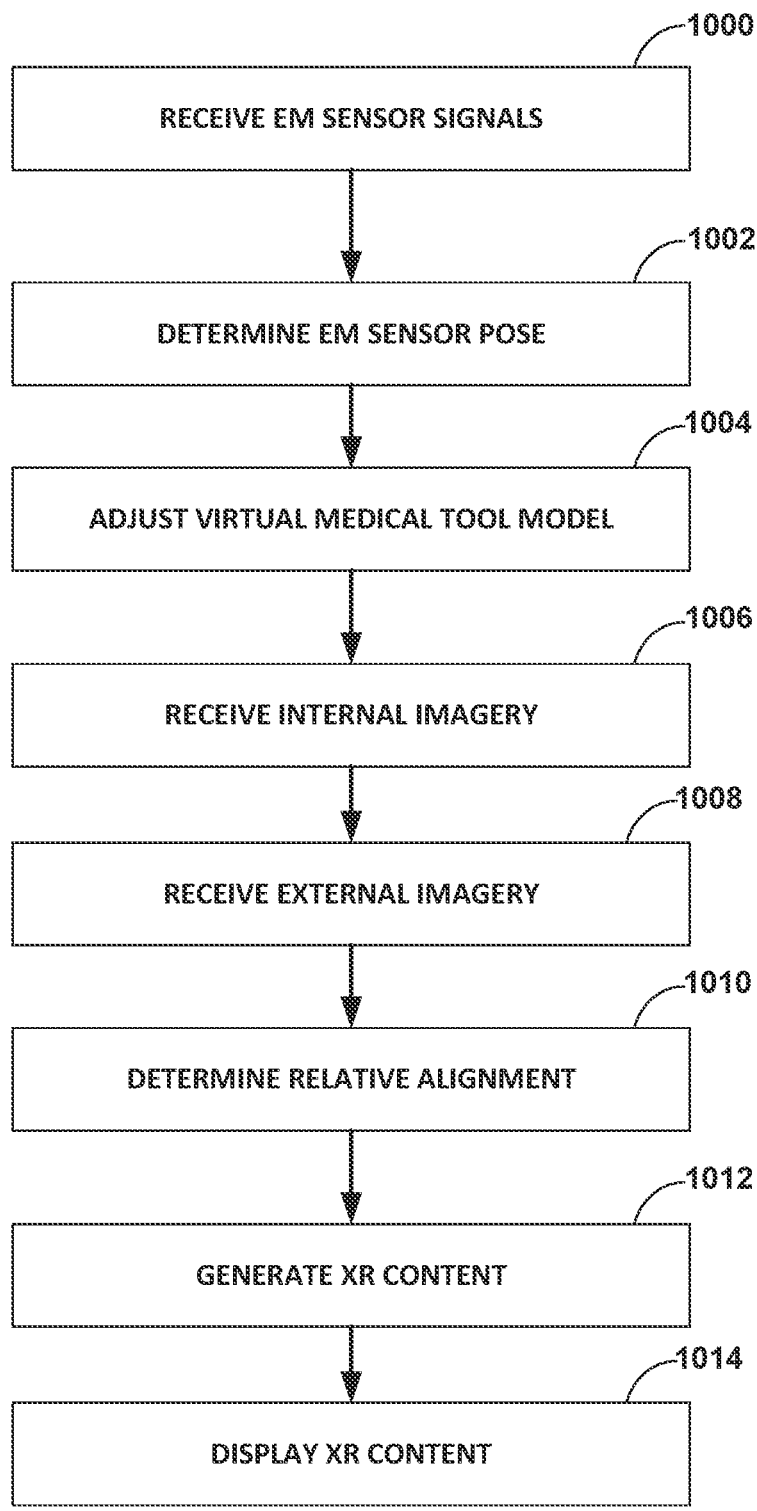
FIG. 10 is a flowchart illustrating an example technique for generating XR content for a medical procedure.

FIG. 10 is a flowchart illustrating example techniques for generating extended-reality (XR) content for a medical procedure. The techniques of FIG. 10 are described with respect to XR system 600 of FIGS. 6A and 6B for purposes of illustration, but may be performed by any suitable XR system in other examples.

A computing device 606, such as processing circuitry of a head-mounted-display (HMD) device 108, receives, from one or more electromagnetic (EM) sensors 604 of an EM sensor system 650, signals indicative of a magnitude of an EM field 624 generated by an EM source 622 of the EM sensor system 650 (1000). For instance, the one or more EM sensors 604 may be disposed at a distal portion of a flexible shaft 614 of a medical tool 602 configured for insertion into a body of a patient 620. As one example application of the techniques of FIG. 10, the medical tool 602 may include a needle for a Transjugular Intrahepatic Portosystemic Shunt (TIPS) procedure.

In response to receiving the EM sensor signals, computing device 606 determines, based on the signals indicative of the magnitude of the EM field 624, a pose of the one or more EM sensors 604 (1002). For instance, the computing device 606 may determine a position and orientation of the EM sensor 604 relative to a known reference point, such as to a base 616 of the medical tool 602, to the EM generator 622, or to another fiducial reference point.

The computing device 606 adjusts a virtual three-dimensional (3-D) model representation 652 of the medical tool 602 based on the determined pose of the one or more EM sensors 604 (1004). For instance, the computing device may determine or estimate a position and orientation of a distal tip of the flexible, elongated shaft 614 of the medical tool relative to the base 616, and by extension, subsequently determine a shape (e.g., a bending or curvature) of the shaft 614 therebetween.

The computing device 606 receives, from an internal imaging device 610, a set of "first" image data or "internal" image data depicting at least a portion of an internal anatomy of the body of a patient 620 (1006). For instance, the computing device 606 may load DICOM data, including X-ray data, MRI data, CT scan data, or any other data depicting a relevant internal anatomy of patient 620. In some examples, but not all examples, the received internal image data may depict or capture an internal imaging target 628 or other fiducial marker, e.g., having one or more known physical parameters.

The computing device 606 receives, from an external imaging device 608 (e.g., a camera of HMD 108), a set of "second" image data or "external" image data depicting at least a portion of the exterior of the body of patient 620 (1008). In some examples, but not all examples, the received external image data may depict or capture an external imaging target 618 or other fiducial marker, e.g., having one or more known physical parameters.

The computing device 606 determines, based on the EM sensor signals, the first image data (e.g., the internal imaging target 628), and the second image data (e.g., the external imaging target 608), a relative alignment between at least two of the three datasets (1010). For instance, computing system 606 may determine a pose (e.g., a relative position and orientation) of the one or more EM sensors 604, a pose of the external imaging target 618, and/or a pose of the internal imaging target 628. Based on the determined relative alignment between these reference points, computing device 606 may determine a relative alignment between the respective datasets as a whole. In some examples herein, a "treble" fiducial marker may constitute a common reference point for aligning all three datasets.

The computing device 606 then generates, based on the determined relative alignment(s) between the reference points and/or the datasets, extended reality (XR) content 612 that includes a visual representation 652 of the medical tool 602 located at the corresponding "real-world" position within a visual representation 654 of at least a portion of the internal anatomy of the patient 620 (1012). The computing device 606 then customizes and outputs the XR content 612 for display on the appropriate XR display device 108 to simulate a current pose of the medical tool relative to the body of the patient (1014). For instance, in examples in which HMD 108 includes a transparent display screen, computing device 606 "registers" and tracks the position of the physical body of patient 620 relative to the transparent display, and displays the XR content 612 on the transparent display at the appropriate real-world position relative to the patient 620. In examples in which HMD 108 includes an opaque display screen, computing device 606 generates composite imagery of the XR content 612 overlaid onto 2-D imagery of the exterior of the patient 620, and outputs the composite imagery for display on the screen.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
   receiving, by processing circuitry and from one or more electromagnetic (EM) sensors of an EM sensor system, signals indicative of a magnitude of an EM field generated by an EM source of the EM sensor system, wherein the one or more EM sensors are disposed at a distal portion of a flexible shaft of a medical tool configured for insertion into a body of a patient;
   determining, by the processing circuitry and based on the signals indicative of the magnitude of the EM field, a pose of the one or more EM sensors;
   adjusting, by the processing circuitry and based on the determined pose of the one or more EM sensors, a three-dimensional (3-D) model representation of the medical tool;
   receiving, by the processing circuitry, first image data depicting at least a portion of an internal anatomy of the body of the patient and an internal imaging target;
   receiving, by the processing circuitry, second image data depicting an external imaging target;
   determining, by the processing circuitry and based on the signals indicative of the magnitude of the EM field, the first image data, and the second image data, a relative alignment between the pose of the one or more EM sensors, a pose of the external imaging target, and a pose of the internal imaging target;
   generating, by the processing circuitry and based on the determined relative alignment, extended reality (XR) content comprising a visual representation of the medical tool within the at least a portion of the internal anatomy of the body; and
   outputting, by the processing circuitry, the XR content for display on an XR device to simulate a current pose of the medical tool relative to the body of the patient.

2. The method of claim 1,
   wherein determining the relative alignment comprises determining, by the processing circuitry, a first relative alignment between the determined pose of the one or more sensors and a pose of the internal imaging target, and
   wherein the method further comprises generating, by the processing circuitry and based on the adjusted 3-D model representation of the medical tool and based on the first relative alignment between the determined pose of the one or more EM sensors and the pose of the internal imaging target, the visual representation of the medical tool within the at least a portion of the internal anatomy of the body.

3. The method of claim 2,
   wherein determining the pose of the one or more EM sensors comprises determining the pose of the one or more EM sensors with respect to an EM coordinate system,
   wherein the method further comprises determining the pose of the internal imaging target with respect to an internal imaging coordinate system, and
   wherein determining the first relative alignment between the pose of the one or more EM sensors and the pose of the internal imaging target comprises determining, based on a predefined distance between the EM sensor system and the internal imaging target, at least one of:
      the pose of the one or more EM sensors with respect to the internal imaging coordinate system; or
      the pose of the internal imaging target with respect to the EM coordinate system.

4. The method of claim 2, wherein determining the relative alignment further comprises determining, by the processing circuitry, a second relative alignment between the pose of the external imaging target and the pose of the internal imaging target.

5. The method of claim 4,
   wherein the method further comprises:
      determining the pose of the internal imaging target with respect to an internal imaging coordinate system; and
      determining the pose of the external imaging target with respect to an external imaging coordinate system,
   wherein determining the second relative alignment between the pose of the external imaging target and the pose of the internal imaging target comprises determining, based on a predefined distance between the internal imaging target and the external imaging target, at least one of:
      the pose of the internal imaging target with respect to the external coordinate system; or
      the pose of the external imaging target with respect to the internal coordinate system.

6. The method of claim 1, wherein the XR device comprises at least one of:
   a head-mounted display (HMD);
   a projector;
   a transparent display;
   a display reflected by a partially reflective surface; or
   a stationary screen-mounted display.

7. The method of claim 1, further comprising positioning the interior imaging target and the exterior imaging target with respect to a rigid portion of the body of the patient, wherein determining the relative alignment comprises determining the relative alignment based at least in part on distances of the interior imaging target and the exterior imaging target from the rigid portion of the body of the patient.

8. The method of claim 7,
   wherein the rigid portion of the body of the patient comprises a bony anatomy of the patient, and
   wherein determining the relative alignment based at least in part on the distances of the interior imaging target and the exterior imaging target from the rigid portion of the body of the patient comprises determining, with the one or more EM sensors, the distances of the interior imaging target and the exterior imaging target from the bony anatomy of the patient.

9. The method of claim 1, wherein the internal imaging target comprises an asymmetrical, radiopaque marker.

10. The method of claim 1,
wherein the method further comprises determining, by the processing circuitry and based on the pose of the one or more EM sensors and the relative alignment, a trajectory of the medical tool through the at least a portion of the internal anatomy, and
wherein generating the XR content comprises generating a visual representation of the trajectory of the medical tool through the at least a portion of the internal anatomy.

11. The method of claim 1, wherein the internal image data comprises CT-scan image data, X-ray image data, fluoroscopy image data, or MRI image data.

12. The method of claim 1, wherein the medical tool comprises a transjugular intrahepatic portosystemic shunt (TIPS) set.

13. The method of claim 1, wherein the second image data further depicts at least a portion of an exterior of the body of the patient.

14. The method of claim 1, wherein the internal imaging target comprises a set of radiopaque markers in an asymmetrical arrangement.

15. The method of claim 1, wherein the internal imaging target comprises an object having at least four points of reference, at least one pair of points has a distance unique from at least five other distances such the at least four points of reference define an unambiguously determinable six-degrees-of-freedom (6DOF) orientation of the internal imaging target in three-dimensional (3-D) space.

16. The method of claim 1, wherein the medical tool comprises a prostate artery embolization catheter.

17. The method of claim 1, wherein the medical tool comprises a microcatheter.

18. The method of claim 1, wherein the medical tool comprises a guidewire.

19. A system comprising processing circuitry configured to:
receive, from one or more sensors of an EM sensor system, signals indicative of a magnitude of an EM field generated by an EM source of the EM sensor system, wherein the one or more EM sensors are disposed at a distal portion of a flexible shaft of a medical tool configured for insertion into a body of a patient;
determine, based on the signals indicative of the magnitude of the EM field, a pose of the one or more EM sensors;
adjust, based on the determined pose of the one or more EM sensors, a three-dimensional (3-D) model representation of the medical tool;
receive first image data depicting at least a portion of an internal anatomy of the body of the patient and an internal imaging target;
receive second image data depicting an external imaging target;
determine, based on the signals indicative of the magnitude of the EM field, the first image data, and the second image data, a relative alignment between the pose of the one or more EM sensors, a pose of the external imaging target, and a pose of the internal imaging target;
generate, based on the determined relative alignment, extended reality (XR) content comprising a visual representation of the medical tool within the at least a portion of the internal anatomy of the body; and
output the XR content for display on an XR device to simulate a current pose of the medical tool relative to the body of the patient.

20. A system comprising:
a medical tool configured for insertion into a body of a patient;
an electromagnetic (EM) sensor system comprising:
an EM source configured to generate an EM field; and
one or more EM sensors configured to generate signals indicative of a magnitude of the EM field, wherein the one or more EM sensors are disposed at a distal portion of a flexible shaft of the medical tool;
processing circuitry configured to:
receive, from the one or more EM sensors, the signals indicative of the magnitude of the EM field;
determine, based on the signals indicative of the magnitude of the EM field, a pose of the one or more EM sensors;
adjust, based on the determined pose of the one or more EM sensors, a three-dimensional (3-D) model representation of the medical tool;
receive first image data depicting at least a portion of an internal anatomy of the body of the patient and an internal imaging target;
receive second image data depicting an external imaging target;
determine, based on the signals indicative of the magnitude of the EM field, the first image data, and the second image data, a relative alignment between the pose of the one or more EM sensors, a pose of the external imaging target, and a pose of the internal imaging target;
generate, based on the determined relative alignment, extended reality (XR) content comprising a visual representation of the medical tool within the at least a portion of the internal anatomy of the body; and
output the XR content for display on an XR device; and
the XR device, where in the XR device is configured to display the XR content to a user to simulate a current pose of the medical tool relative to the body of the patient.

* * * * *